# (12) United States Patent
Smith et al.

(10) Patent No.: US 8,367,318 B2
(45) Date of Patent: Feb. 5, 2013

(54) SCREENING OF MICRO-RNA CLUSTER INHIBITOR POOLS

(75) Inventors: Anja Smith, Thornton, CO (US); Scott Baskerville, Louisville, CO (US); Devin Leake, Denver, CO (US); Annaleen Vermeulen, Lafayette, CO (US); Barbara Robertson, Boulder, CO (US); Anastasia Khvorova, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 202 days.

(21) Appl. No.: 12/670,363

(22) PCT Filed: Jul. 21, 2008

(86) PCT No.: PCT/US2008/070606
§ 371 (c)(1),
(2), (4) Date: Jun. 15, 2010

(87) PCT Pub. No.: WO2009/015071
PCT Pub. Date: Jan. 29, 2009

(65) Prior Publication Data
US 2010/0273856 A1    Oct. 28, 2010

Related U.S. Application Data

(60) Provisional application No. 60/951,361, filed on Jul. 23, 2007.

(51) Int. Cl.
*C12Q 1/68*    (2006.01)
(52) U.S. Cl. .............................. 435/6; 435/325; 435/375
(58) Field of Classification Search .................. None
See application file for complete search history.

(56) References Cited

U.S. PATENT DOCUMENTS

| 2005/0147608 A1 | 7/2005 | Ryo et al. |
| 2007/0072204 A1* | 3/2007 | Hannon et al. .................... 435/6 |
| 2009/0291907 A1* | 11/2009 | Esau et al. ....................... 514/44 |

FOREIGN PATENT DOCUMENTS

| WO | WO 00/73802 A1 | 12/2000 |
| WO | WO 01/16168 A2 | 3/2001 |
| WO | WO 2007/081740 A2 | 7/2007 |

OTHER PUBLICATIONS

Si, et al. (2007) miR-21-mediated Tumor Growth., Oncogene, v.26:2799-803.*
Low, et al. (2007) High-Content Imaging Analysis of the Knockdown Effects of Validated siRNAs and Antisense Oligonucleotides, Journal of Biomolecular Screening, v.12:775-88.*
Ventura et al. (Cell 132, 875-886; Mar. 7, 2008).*

* cited by examiner

*Primary Examiner* — Kimberly Chong
(74) *Attorney, Agent, or Firm* — Dorf & Nelson LLP; Scott D. Locke, Esq.

(57) ABSTRACT

The disclosure provides methods for inhibiting the activity of a miRNA cluster in a cell, and also for screening a cell for a phenotype(s) of interest resulting from inhibition of a miRNA cluster. The methods use a cluster pool which comprises at least one miRNA inhibitor specific for each miRNA in the miRNA cluster. MiRNA inhibitors are described that induce apoptosis in breast cancer cells and hence are useful in the treatment of breast cancer. The disclosure also provides pharmaceutical compositions which are useful for the treatment of breast cancer; methods for inducing the nuclear translocation of NF-κB in a breast cancer cell; methods for inducing the nuclear translocation of c-Jun in a breast cancer cell; method for inhibiting the nuclear translocation of NF-κB in a breast cancer cell; and methods for providing prognostic medical information relating to breast cancer progression.

10 Claims, 19 Drawing Sheets"

| Cluster | Object count ↓ | c-Jun ↑ | NF-κB↑ | NF-κB ↓ |
|---|---|---|---|---|
| (D6) miR-17-5p, 18a, 19a, 20a, 19b, 92 | √ | √ | √ | |
| (A3) miR-93, 106b, 25 | √ | √ | √ | |
| (B3) miR-16, 15a | √ | | | |
| (C5) miR-200b, 200a, 429 | √ (96hrs) | √ (96hrs) | | |
| (C2) miR-30b, 30d | √ (96hrs) | √ (96hrs) | | |
| (E3) miR-141, 200c | √ (96hrs) | √ (96hrs) | | |
| (E1) miR-502, 501, 500, 362, 188 | √ (96hrs) | √ (96hrs) | | |
| (B2) miR34b, 34c | √? | √ | | |
| (C4) miR-30e-5p, 30c | | √ | | |
| (A5) miR-195, 497 | | | | √? |

SCREENING OF MICRO-RNA CLUSTER INHIBITOR POOLS

RELATED APPLICATION INFORMATION

This application is a National Stage Application of PCT/US2008/070606 which was filed on 21 Jul. 2008, in the name of Dharmacon, Inc., a U.S. national corporation, applicant for the designation of all countries except the U.S., and Anja SMITH, a citizen of the U.S., Scott BASKERVILLE, a citizen of the U.S., Devin LEAKE, a citizen of the U.S., Annaleen VERMEULEN, a citizen of the U.S., Barbara ROBERTSON, a citizen of the U.S., and Anastasia KHVOROVA, a citizen of Russia, applicants for the designation of the U.S. only, and claims priority to U.S. Provisional Patent Application Ser. No. 60/951,361 filed on 23 Jul. 2007, and which applications are incorporated herein by reference. To the extent appropriate, a claim of priority is made to each of the above disclosed applications.

FIELD OF THE INVENTION

The present disclosure relates to the use of miRNAs and miRNA inhibitors, particularly to the use of cluster pools comprising at least one miRNA inhibitor for each miRNA in a particular miRNA cluster.

BACKGROUND

RNA interference (RNAi) is a near-ubiquitous pathway involved in post-transcriptional gene modulation. A key effector molecule of RNAi is the microRNA (miRNA or miR). These small, non-coding RNAs are transcribed as primary miRNAs (pri-miRNA) and processed in the nucleus by Drosha (a Type III ribonuclease) to generate short hairpin structures referred to as pre-miRNAs. The resulting molecules are transported to the cytoplasm and processed by a second nuclease (Dicer) before being incorporated into the RNA Induced Silencing Complex (RISC). Interactions between the mature miRNA-RISC complex and messenger RNA (mRNA), particularly between the seed region of the miRNA guide strand (nucleotides 2-7) and regions of the 3' UTR of the mRNA, leads to gene knockdown by transcript cleavage and/or translation attenuation.

MicroRNAs frequently occur in clusters on chromosomes. MicroRNA clusters fall into two distinct categories: clusters where the individual miRNAs are derived from processing of a common (polycistronic) transcript, and clusters where the individual miRNAs are not derived from a common transcript but are instead co-transcribed because they are regulated by common factors. Using distance-based criteria, 46 miRNA clusters have been identified, containing a total of about 110 miRNAs. The functional relevancy of the clustering of microRNAs has not been adequately established by prior art techniques.

SUMMARY OF THE DISCLOSURE

In one aspect, the disclosure provides a method for inhibiting the activity of a miRNA cluster in a cell (in vitro or in vivo, e.g. in a human). The method comprises introducing into the cell a cluster pool comprising at least one miRNA inhibitor specific for each miRNA in the miRNA cluster.

In another aspect, the disclosure provides methods for screening a cell for a phenotype(s) resulting from inhibition of a miRNA cluster. The methods comprise introducing into the cell a cluster pool which comprises at least one miRNA inhibitor specific for each miRNA in the miRNA cluster. A determination is then made as whether the cell manifests the phenotype(s). In some embodiments, the methods further comprise the step of determining whether the phenotype(s) can be recapitulated in the cell by an individual miRNA inhibitor from the cluster pool. This may be achieved by introducing into the cell an individual miRNA inhibitor from the cluster pool (optionally at a plurality of different concentrations) and then determining whether the cell manifests the phenotype(s).

In some embodiments, the phenotype(s) detected include at least one of increased cell death, decreased cell death, increased c-Jun nuclear translocation, decreased c-Jun nuclear translocation, increased NF-κB nuclear translocation, and decreased NF-κB nuclear translocation (all relative to cells that are not treated with the miRNA inhibitors).

In some embodiments, the phenotype(s) of interest are determined using High Content Screening (HCS).

In some embodiments, the cells into which the cluster pool is introduced are breast cancer cells, including but not limited to MCF7 breast cancer cells.

In another aspect, the disclosure provides methods for inducing apoptosis in a breast cancer cell. The methods involve introducing into a breast cancer cell (in vitro, or in vivo, e.g. in a breast cancer patient) at least one miRNA inhibitor selected from the group consisting of a miR-17-5p inhibitor, a miR-106b inhibitor, a miR-15a inhibitor, a miR-16 inhibitor, a miR-200b inhibitor, a miR-200a inhibitor, a miR-429 inhibitor, a miR-30b inhibitor, a miR-30d inhibitor, a miR-141 inhibitor, a miR-200c inhibitor, a miR-502 inhibitor, a miR-501 inhibitor, a miR-500 inhibitor, a miR-362 inhibitor, a miR-188 inhibitor, a miR-34b inhibitor, and a miR-34c inhibitor.

In another aspect, the disclosure provides pharmaceutical compositions which are useful for the treatment of breast cancer. The pharmaceutical compositions comprise at least one miRNA inhibitor selected from the group consisting of a miR-17-5p inhibitor, a miR-106b inhibitor, a miR-15a inhibitor, a miR-16 inhibitor, a miR-200b inhibitor, a miR-200a inhibitor, a miR-429 inhibitor, a miR-30b inhibitor, a miR-30d inhibitor, a miR-141 inhibitor, a miR-200c inhibitor, a miR-502 inhibitor, a miR-501 inhibitor, a miR-500 inhibitor, a miR-362 inhibitor, a miR-188 inhibitor, a miR-34b inhibitor, and a miR-34c inhibitor and further comprise at least one pharmaceutically acceptable excipient.

In another aspect, the disclosure describes the use of at least one miRNA inhibitor selected from the group consisting of a miR-17-5p inhibitor, a miR-106b inhibitor, a miR-15a inhibitor, a miR-16 inhibitor, a miR-200b inhibitor, a miR-200a inhibitor, a miR-429 inhibitor, a miR-30b inhibitor, a miR-30d inhibitor, a miR-141 inhibitor, a miR-200c inhibitor, a miR-502 inhibitor, a miR-501 inhibitor, a miR-500 inhibitor, a miR-362 inhibitor, a miR-188 inhibitor, a miR-34b inhibitor, and a miR-34c inhibitor for the manufacture of a medicament for the treatment of breast cancer.

In another aspect, the disclosure provides methods for inducing the nuclear translocation of NF-κB in a breast cancer cell. The method comprise introducing into a breast cancer cell (in vitro or in vivo, e.g, in a human) at least one miRNA inhibitor selected from the group consisting of a miR-17-5p inhibitor, a miR-106b inhibitor, and a miR-93 inhibitor.

In another aspect, the disclosure provides methods for inducing the nuclear translocation of c-Jun in a breast cancer cell. The methods comprise introducing into a breast cancer cell (in vitro or in vivo, e.g, in a human) at least one miRNA inhibitor selected from the group consisting of a miR-17-5p inhibitor, a miR-106b inhibitor, a miR-93 inhibitor, a miR-30e-5p inhibitor, a miR-200b inhibitor, a miR-200a inhibitor, a miR-429 inhibitor, a miR-30b inhibitor, a miR-30d inhibitor, a miR-141 inhibitor, a miR-200c inhibitor, a miR-502 inhibitor, a miR-501 inhibitor, a miR-500 inhibitor, a miR-362 inhibitor, a miR-188 inhibitor, a miR-34b inhibitor, and a miR-34c inhibitor.

In another aspect, the disclosure provides a method for inhibiting the nuclear translocation of NF-κB in a breast cancer cell. The method comprises introducing into a breast cancer cell (in vitro or in vivo, e.g, in a human) at least one miRNA inhibitor selected from the group consisting of a miR-195 inhibitor and a miR-497 inhibitor.

In another aspect, the disclosure provides methods for providing prognostic medical information relating to breast cancer progression in an individual known or suspected to have breast cancer. The methods comprise determining in a biological sample from an individual the expression level of at least one miRNA selected from the group consisting of miR-17-5p, miR-106b, miR-15a, miR-16, miR-200b, miR-200, miR-429, miR-30b, miR-30d, miR-141, miR-200c, miR-502, miR-501, miR-500, miR-362, miR-188, miR-34b, and miR-34c. Since inhibitors of the aforementioned miRNAs induce apoptosis of breast cancer cells, a low level of expression of at least one of the aforementioned miRNAs is correlated with an improved prognosis relative to an individual with a higher level of expression.

Further aspects and embodiments of the invention are provided herein.

BRIEF DESCRIPTION OF THE FIGURES

FIG. 17 provides a summary of the hits and the phenotypes they are associated with when inhibited.

DETAILED DESCRIPTION OF THE EMBODIMENTS

Figure 1:
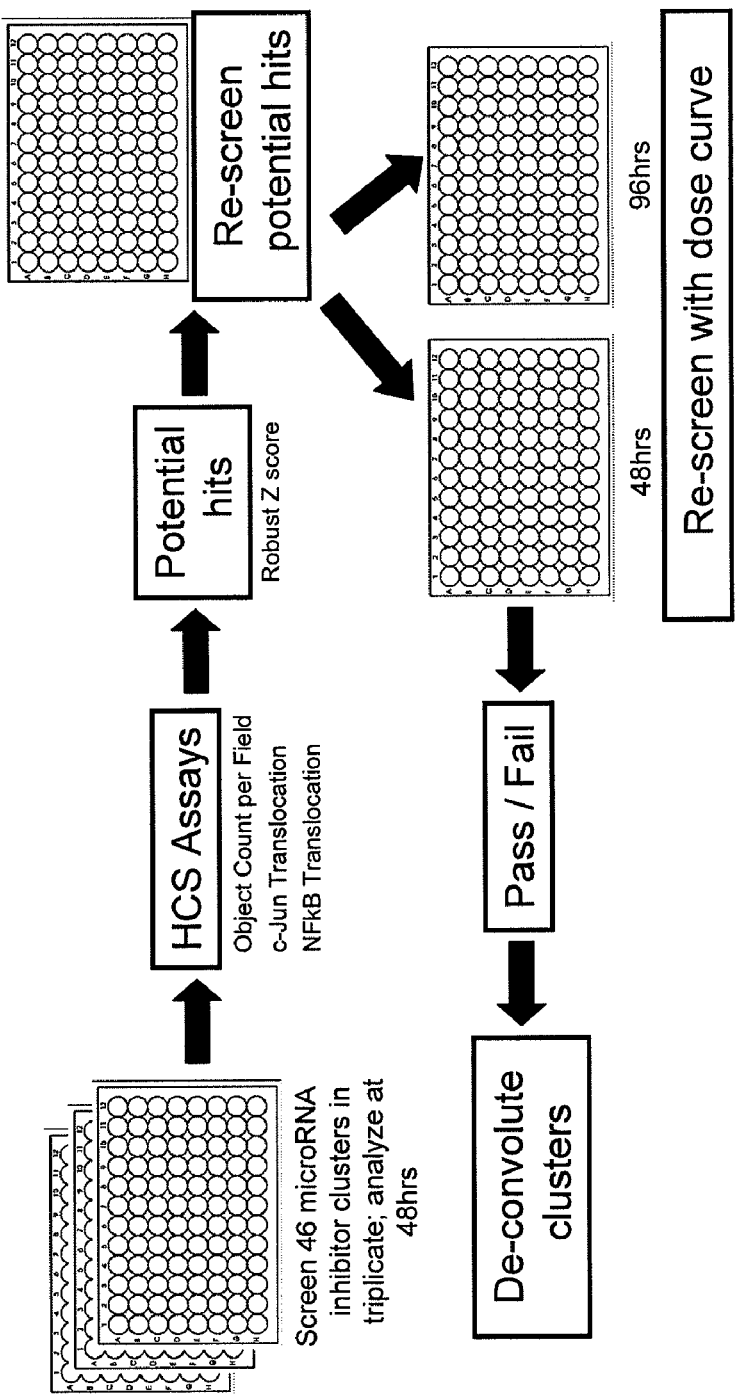
FIG. 1 shows schematically an example of a HCS-based cluster pool screen according to the disclosure. In this example, cells in multiwell plates are transfected with the 46 miRNA cluster pools in triplicate, incubated for 48 hours (one cluster pool/well), and then screened for relevant phenotypes using HCS. Potential hits (e.g. cluster pools that provide relevant phenotypes) are rescreened at 48 hours and 96 hours following transfection with varying doses of the cluster pools. Cluster pools which continue to provide relevant phenotypes in the rescreening process are then deconvoluted in order to determine which individual miRNA inhibitors are responsible for the observed phenotypes.

All sequences in this disclosure are provided in 5' to 3' orientation unless otherwise stated. All references cited herein are incorporated by reference in their entirety.

The term "mature strand" refers to the strand of a fully processed miRNA, or an siRNA that enters RISC. In some cases, miRNAs have a single mature strand that can vary in length between about 17-28 nucleotides in length. In other instances, miRNAs can have two mature strands (i.e. two unique strands that can enter RISC), and the length of the strands can vary between about 17 and 28 nucleotides. In the present disclosure, the terms "mature strand," "guide strand" and "antisense strand" are used interchangeably.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses→humans) and have been shown to play a role in development, homeostasis, and disease etiology.

The terms "microRNA inhibitor", "miR inhibitor", or "inhibitor" are synonymous and refer to oligonucleotides or modified oligonucleotides that interfere with the ability of specific miRNAs, or siRNAs to silence their intended targets. Inhibitors can adopt a variety of configurations including single stranded, double stranded (RNA/RNA or RNA/DNA duplexes), and hairpin designs. miRNA inhibitors can also include modified nucleotides including but not limited to 2'-O-methyl and 2'-F modified nucleotides and Locked Nucleic Acid (LNA) modified molecules. In general, microRNA inhibitors comprise a nucleic acid that is at least partially the reverse complement of a mature miRNA sequence. In addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl)methoxy)-3 hydroxypentylcarbamate) which allows passive uptake a micro-RNA inhibitor into a cell. Micro-RNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 16 and 31 nucleotides and chemical modification patterns can comprise one or more of the following: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang. Mimics can also comprise linker conjugate modifications that enhance stability, delivery, specificity, functionality, or strand usage.

The term "miRNA seed" or "seed" refers to a region of the mature strand(s) of a microRNA or microRNA mimic. The region generally includes nucleotides 2-6 or 2-7 counting from the 5' end of the mature strand.

The term "miRNA seed complement" or "seed complement" refers to a sequence of nucleotides in a target gene, preferably in the 3' UTR of a target gene, that is complementary to some or all of the miRNA seed.

The term "gene silencing" refers to a process by which the expression of a specific gene product is lessened or attenuated by RNA interference. The level of gene silencing (also sometimes referred to as the degree of "knockdown") can be measured by a variety of means, including, but not limited to, measurement of transcript levels by Northern Blot Analysis, B-DNA techniques, transcription-sensitive reporter constructs, expression profiling (e.g. DNA chips), qRT-PCR and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g., GFP) or enzymatic activity (e.g. alkaline phosphatases), or several other procedures.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoai nleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

The term "polynucleotide" refers to polymers of two or more nucleotides, and includes, but is not limited to, DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

The term "ribonucleotide" and the term "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

The term "RNA interference" and the term "RNAi" are synonymous and refer to the process by which a polynucleotide (a miRNA or siRNA) comprising at least one polyribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

The term "siRNA" and the phrase "short interfering RNA" refer to unimolecular nucleic acids and to nucleic acids comprised of two separate strands that are capable of performing RNAi and that have a duplex region that is between 14 and 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

siRNAs can be duplexes, and can also comprise short hairpin RNAs, RNAs with loops as long as, for example, 4 to 23 or more nucleotides, RNAs with stem loop bulges, microRNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms. When the siRNAs are hairpins, the sense strand and antisense strand are part of one longer molecule.

Detailed descriptions of the criteria for the rational design of siRNA antisense strands for efficient gene silencing can be found in WO 2004/045543, WO 2006/006948, WO 2005/078095, WO 2005/097992, and WO 2005/090606.

siRNAs can target any sequence including protein encoding sequences (e.g., open reading frames, ORFs), and non-coding sequences (e.g., 3' UTRs, 5' UTRs, intronic regions, promoter regions, microRNAs, piRNAs, enhancer regions, repetitive sequences, and more). In contrast, microRNA and piRNA mimics of the disclosure generally target a subset of genes and tools for predicting miRNA targets can be found in any number of publications including but not limited to Griffith-Jones, S. et al., Nucleic Acids Research, 2007.

The term "piRNAs" refers to Piwi-interacting RNAs, a class of small RNAs that are believed to be involved in transcriptional silencing (see Lau, N. C. et al (2006) *Science*, 313:305-306).

In one embodiment, the methods of the disclosure involve introducing into cells (e.g., by transfection, passive uptake etc) a cluster pool comprising a plurality of miRNA inhibitors. The cluster pool comprises at least one miRNA inhibitor for each miRNA in a particular cluster. For example, if a miRNA cluster contains five different miRNAs, then a cluster pool would comprise at least five different miRNA inhibitors, each one specific for one of the miRNAs in the cluster. As a result of introduction of the cluster pool into the cell, the activity of the entire miRNA cluster is effectively inhibited.

Cells into which a cluster pool has been introduced may then screened for phenotypes, including, for example, phenotypes that are relevant to disease development and progression. In some embodiments, a cluster pool is introduced into cells, and the cells are then incubated for a predetermined period of time prior to assaying for phenotypes of interest. Cluster pools that yield phenotypes of interest are preferably rescreened to confirm the initial results. Rescreening may be performed using the same incubation time as the initial screen, and/or using a longer and/or shorter incubation time than in the initial screen. For example, an initial screen may involve incubating cells for 48 hours following the introduction of a cluster pool, then rescreening by incubating cells for both 48 hours and 96 hours following introduction of a cluster pool. In some embodiments, the initial screen may be performed at a plurality of time points e.g. by incubating cells for 24 hours, 48 hours, and 96 hours following introduction before assaying for phenotype(s). A cluster pool that is identified as causing a phenotype(s) of interest may also be rescreened at a variety of different concentrations in order to establish a dose-response curve.

Once a cluster pool has been identified that yields a phenotype(s) of interest, the individual miRNA inhibitors in the pool can be tested individually, or in combination with other inhibitors in the pool, in order to deconvolute the cluster pool i.e. to determine which miRNA(s) are responsible for the observed phenotype(s). In some cases, a single miRNA inhibitor will recapitulate a phenotype of the pool of miRNA inhibitors; in other cases, a phenotype will be observed only when all miRNAs in the cluster are inhibited; and in other cases, a phenotype will be observed when less than all miRNAs in the cluster are inhibited. When a plurality of phenotypes are observed for a cluster pool, then different miRNAs in the cluster pool may be responsible for different phenotypes.

In some embodiments, the individual miRNA inhibitors are present at equimolar concentrations in the cluster pool. During the deconvolution studies, each miRNA inhibitor may be tested at the concentration at which it is present in the cluster pool, or at a higher concentration. For example, if miRNA cluster contains five miRNAs, then a corresponding cluster pool would contain five miRNA inhibitors (one for each miRNA) at equimolar concentrations. If the total concentration of miRNA inhibitors in the pool was 50 nM, then each individual miRNA would be present at 10 nM. If a phenotype can be recapitulated using an individual miRNA inhibitor at the same concentration it is present at in the cluster pool, then this indicates that the miRNA inhibitor is responsible for the phenotype observed with the cluster pool. If a phenotype can be recapitulated with an individual miRNA but only at a higher concentration than it is present in the cluster pool, then this indicates that the phenotype is the result of a synergistic or dosing effect with other miRNA inhibitors in the cluster pool. If no individual miRNA inhibitors in a cluster pool can recapitulate a phenotype, this indicates that a plurality of miRNA inhibitors in the cluster pool work synergistically to produce the phenotype.

In some embodiments, High Content Screening (HCS) is used to assay for a plurality of phenotypes in cells using a plurality of cluster pools (e.g. each cluster pool specific for a particular miRNA cluster) in a single experiment. HCS uses automated fluorescence microscopy and image analysis techniques to rapidly collect spatial and temporal fluorescence data from cells in a multiwell format. For example, HCS can be used to determine the concentration and/or subcellular location of proteins (e.g. fluorescently-labeled proteins) which are thought to be implicated in disease. In addition, cell viability and cell morphology data can be acquired during HCS. Changes in any of the observed characteristics of the cells transfected with cluster pools relative to appropriate controls are considered to be phenotypes indicative of a response to the cluster pool. Commercial HCS systems are available such as the ArrayScan V system from Cellomics.

An example of a HCS-based cluster pool screen according to the disclosure is presented schematically in FIG. 1. In this example, cells in multiwell plates are transfected with the 46 miRNA cluster pools in triplicate, incubated for 48 hours (one cluster pool/well), and then screened for relevant phenotypes using HCS. Potential hits (e.g. cluster pools that provide relevant phenotypes) are rescreened at 48 hours and 96 hours following transfection with varying doses of the cluster pools. Cluster pools which continue to provide relevant phenotypes in the rescreening process are then deconvoluted in order to determine which individual miRNA inhibitors are responsible for the observed phenotypes.

The embodiments discussed above use cells in vitro to screen a pool of miRNA cluster inhibitors for relevant phenotypes, followed by the deconvolution of the pool of inhibitors to determine which inhibitor(s) are responsible for the phenotype of interest. One skilled in the art will also recognize that the methods disclosed herein may also be used with isolated tissues in vitro, and also with whole organisms including, but not limited to, *Drosophila melanogaster, Caenorhabditis elegans*, and mammals (e.g. mice, rats, humans). In whole organisms, the individual members of a cluster pool may be expressed either throughout the organism or in a particular cell-type or tissue type using, for example, techniques for the expression of exogenous sequences that are well known in the art.

The methods of the disclosure allow the inhibition of the activity of a miRNA cluster in a cell by introducing into the cell a cluster pool comprising at least one miRNA inhibitor specific for each miRNA in the miRNA cluster. By initially screening for relevant phenotypes using cluster pools, the methods of the disclosure also allow the skilled person to identify phenotypes that are the result of the inhibition of multiple miRNAs. Such phenotypes would likely not be observed if single miRNA inhibitors were used instead of cluster pools.

Uses of the miRNAs and miRNA Inhibitors Identified According to the Methods of the Disclosure Cluster miRNAs (along with their corresponding pri-miRNAs and pre-miRNAs) that are identified by the methods of the disclosure may be used as diagnostic and prognostic markers for diseases in which the phenotypes using in the screening methods are implicated. For example, if the inhibition of a particular miRNA cluster member(s) leads to a phenotype that is correlated with a good prognosis for a specific disease (e.g., inhibition of miR-17-5p is correlated with apoptosis of breast cancer cells, as described below), then this suggests that individuals with a relatively high level of expression of the miRNA cluster member(s) may have a worse prognosis for the specific disease than individuals with a relatively low level of expression of the miRNA cluster. Conversely, if the inhibition of a particular miRNA cluster leads to a phenotype that is correlated with a poor disease prognosis, then this suggests that individuals with a high level of expression of the miRNA cluster may have a better prognosis than individuals with a relatively low level of expression of the miRNA cluster.

A range of techniques well known in the art can be used to quantitate amounts of one or more cluster miRNAs from e.g., a biological sample in order to perform the abovementioned diagnostic or prognostic assays. For instance, complements of the mature miRNA sequences of the disclosure can be associated with a solid support (e.g., a microarray) and purified RNA from e.g., clinical or control samples can be fluorescently labeled and profiled to determine whether a patient is suffering from cancer or a related disease (see Baskerville, S. et al. RNA 11:241-7). One preferred microarray platform is described in the document in WO/2008/048342 which is incorporated herein by reference. Alternatively, quantitative PCR-based techniques can be used to assess the relative amounts of any of the miRNAs of the disclosure derived from e.g., control and/or test samples (Duncan, D. D. et al. 2006 Anal. Biochem. 359:268-70).

Preferably, statistical methods are used to identify significant changes in miRNA levels for the aforementioned prognostic and diagnostic assays. For example, in one embodiment, p values are calculated using known methods to determine the significance in the change of the level of expression of a miRNA. In some embodiments, a value of p<0.05 is used as a threshold value for significance.

MicroRNA inhibitors and cluster miRNAs (along with their corresponding pri-miRNAs and pre-miRNAs) that are identified by the methods of the disclosure may also be used to design and identify therapeutic agents. If a particular phenotype observed following transfection with a cluster pool (or an individual miRNA(s) obtained by deconvoluting a pool) is correlated with disease progression or development, then this indicates that a synthetic miRNA (e.g. a mimic) would be a useful therapeutic. Conversely, if a particular phenotype observed following transfection with a cluster pool (or an individual miRNA(s) obtained by deconvoluting a pool) is correlated with an improved prognosis for a disease (e.g., an inhibitor of miR-17-5p leads to apoptosis in breast cancer cells, as described below), then this would suggest that miRNA inhibitors (e.g., a cluster pool, a single miRNA inhibitor, or a plurality of miRNA inhibitors) may be useful as therapeutic agents for the treatment of disease. Such agents can be used individually, in combination with other miRNA mimics or inhibitors described herein (e.g. with other cluster pools), in combination with miRNAs mimics or inhibitors previously described, or in combination with other agents (e.g., small molecules). Therapeutic miRNA inhibitors of the disclosure can adopt a wide range of designs. In one instance, inhibitors are short (21-31 nucleotide) single stranded, and heavily 2'-O-alkyl modified molecules (see Krutzfeldt et al. 2005. Nature. 438(7068):685-9). Alternatively, miRNA inhibitors of the disclosure can utilize more advanced elongated, double stranded, or hairpin designs which are described in detail in WO2007/095387 and WO 2008/036825. Like synthetic miRNA mimics, inhibitor molecules can be modified with a wide range of chemical modifications to enhance stability, functionality, cellular uptake, and specificity, and can be delivered using an array of techniques including lipid mediated delivery, electroporation, and expression based systems (see, for instance, Ebert, M. S. et al. 2007 Nature Methods. 4: 721-6). In some embodiments, the inhibitor is conjugated to a lipid molecule such as cholesterol (preferably using a linker) in order to allow passive delivery of the inhibitor to a cell. See WO 2008/036825.

In some instances, genomic amplification of a miRNA cluster in a tissue may result in a higher level of expression of one or more miRNAs in that cluster relative to tissues in which the miRNA cluster has not undergone amplification. Thus, in another embodiment, the copy number of a miRNA cluster (which has been implicated in a disease state according to the screening methods disclosed herein) is measured in a tissue suspected of being diseased. If the cluster pool analysis methods of the disclosure indicate that a high level of expression of one or more miRNAs in a miRNA cluster is correlated with a disease state, then an amplification of the miRNA cluster in the suspect tissue relative to a control tissue indicates that the suspect tissue is diseased. Methods suitable for determining the genomic copy number of a miRNA cluster include Southern blotting, fluorescence in situ hybridization, comparative genomic hybridization, and amplification based methods such as quantitative PCR (for example, using Taqman probes).

Therapeutic agents that mimic the effect of a particular miRNA inhibitor or miRNA may be obtained by, for example, screening candidate drug libraries for molecules that replicate a phenotype observed using a miRNA inhibitor(s).

Pharmaceutical compositions comprising the inhibitors, mimics, siRNAs, and small molecules of the disclosure are also expressly contemplated and may be used for the treatment or prevention of diseases that are correlated with the phenotypes used in the screening methods through which the relevant cluster miRNAs were identified. Such pharmaceutical formulations preferably also comprise one or more pharmaceutically acceptable carriers or excipients, and may be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the therapeutic compositions of the invention can be formulated in liquid solutions, preferably in physiologically compatible buffers such as Hank's solution or Ringer's solution. In addition, the therapeutic compositions may be formulated in solid form and redissolved or suspended immediately prior to use. Lyophilized forms are also included. Preparations for oral administration are also contemplated, and may be formulated in a conventional manner to give either immediate or controlled release.

In addition to their use in vivo, the inhibitors, mimics, siRNAs, and small molecules of the disclosure can be delivered to cells ex vivo. Synthetic mimics and inhibitors can be delivered to cells by a variety of methods including, but not limited to, lipid (e.g. DharmaFECT1, Thermo Fisher Scientific) or chemical (e.g. calcium phosphate) mediated transfection, electroporation, lipid-independent delivery via conjugation to one or more entities that mediate lipid- or chemical-independent delivery (e.g. conjugation of cholesterol), or any other method that has been identified or will be identified for nucleic acid transfer to target cells.

In addition, mimics and inhibitors can be delivered to a cell using a plasmid vector that expresses the sequence(s) that encode the mimic or inhibitor of choice. Such expression vectors can be introduced into cells (including cells within an organism such as a human being) by art-recognized transfection methods (e.g. Lipofectamine 2000, Invitrogen) or via viral-mediated delivery (e.g. lentiviral, adenoviral).

Extensive studies into the mechanism of miRNA action have identified characteristic features of miRNA target genes. These include the presence of the 3' UTR target sites (e.g. seed complements), the number and positioning of seed complements within a 3' UTR, preferences for local AU-rich sequences and more (see, for instance, Grimson, A. et al 2007. Mol Cell 27:91-105). As such, target genes can be identified bioinformatically (e.g., see the miRNA target prediction site at http://www.russell.embl-heidelberg.de/miRNAs/; Targetscan, http://www.targetscan.org/mamm_31/), by microarray analysis (Huang et. al., 2007, Nature Methods 4:1045-9), and by biochemical methods (Karginov, F. V., 2007, PNAS 104:19291-6). Thus, the target genes of cluster miRNAs identified by the methods disclosed herein (e.g., the miRNAs identified below that are implicated in breast cancer cell apoptosis, such as miR-17-5p) may themselves be identified, and the target genes (e.g. mRNA from a target gene) may themselves serve as diagnostic or prognostic markers for disease. A range of techniques known in the art can be used to quantitate the expression level of a target gene from e.g., a biological sample. In some embodiments, the mRNA produced by a target gene is measured using, for example, PCR-based methods (e.g., quantitative PCR), microarray-based methods, Northern blotting, or any other technique known in the art for measuring the level of mRNA. In other embodiments, the level of the protein encoded by the target gene is measured using, for example, western blots, antibody arrays, ELISA assays, or any other technique known in the art. Moreover, the target genes may also be used as therapeutic targets for the treatment of disease (e.g. a siRNA specific for a target gene would be a useful therapeutic agent if decreased expression of the target gene is correlated with an improved prognosis).

In another embodiment, target genes can be used as molecular markers in drug screening assays during drug development. Typically, in the early stages of drug development, in vitro studies involving cultured cells that often mimic one or more aspects of diseased tissue are performed to identify molecules that induce desirable phenotypes. In one preferred example, one or more of the targets of a miRNA(s) identified by the methods disclosed herein are used to screen a collection of small molecules to identify agents that modulate the expression of the target gene. Agents that cause e.g., target expression levels to return to a level that is more normal would be considered potential therapeutic candidates.

In another example, one or more target genes are used as prognostic indicators to judge the effectiveness of drug treatment regimes. For example, the levels of miRNA targets of the disclosure can be assessed in patients receiving a particular treatment to determine the effectiveness of the treatment in lessening one or more phenotypes of the disease.

Synthetic, therapeutic miRNAs (microRNA mimics) or miRNA inhibitors can be generated using a range of art-recognized techniques (e.g. ACE chemistry, see U.S. Pat. Nos. 6,111,086; 6,590,093; 5,889,136; and 6,008,400) and introduced into cells by any number of methods including electroporation-mediated delivery, lipid-mediated delivery, or conjugate-mediated delivery (including but not limited to cholesterol or peptide-mediated delivery). In still other instances, therapeutic miRNAs and inhibitors can be delivered using a vector (e.g., plasmid) or viral (e.g., lentiviral) expression system. One preferred expression system is described in PCT/US2008/64462. Studies have demonstrated that not all miRNAs are processed with equal efficiency. For that reason, incorporation of the therapeutic miRNAs of the disclosure into a highly processed scaffold (e.g., miR-196a-2) would ensure efficient processing and expression.

Therapeutic miRNAs and inhibitors of the disclosure can contain modifications that enhance functionality, specificity, cellular uptake, strand usage, and stability. For instance, studies presented in U.S. patent application Ser. No. 11/051,195 and other documents have identified multiple chemical modification patterns, including 2'-O-methyl modifications, locked nucleic acids (LNAs), morpholinos, ethylene-bridged analogs (ENAs), 2'-F modifications, and phosphorothioate modifications, that greatly enhance the stability of double stranded RNAs in serum. Similarly, addition of 2'-O-methyl modifications to positions 1 and 2 (counting from the 5' end of the molecule) in the passenger strand can enhance functionality and specificity (see patent application Ser. No. 11/019,831).

In preferred embodiments, the therapeutic miRNAs and inhibitors contain the modification patterns and conjugate moieties disclosed in WO 2008/036825. For example, in one embodiment, a miRNA mimic of the disclosure comprises an RNA duplex having:

1. a sense strand that ranges in size from about 18 to about 30 nucleotides wherein nucleotides 1 and 2 (numbered from the 5' end) are 2' O-methyl modified and wherein all C nucleotides and all U nucleotides are 2'O-methyl modified;
2. an antisense strand that ranges in size from about 18 to about 30 nucleotides, wherein all C nucleotides and all U nucleotides are 2' F modified, and wherein the antisense strand has significant levels of complementarity to the sense strand as well as to the target gene of the endogenous miR;
3. a 2 nucleotide overhang at the 3' end of the antisense strand comprising phosphorothioate linkages;
4. a cholesterol molecule attached to the 3' end of the sense strand via a C5 linker molecule wherein the cholesterol-linker-sense strand can have the structure:

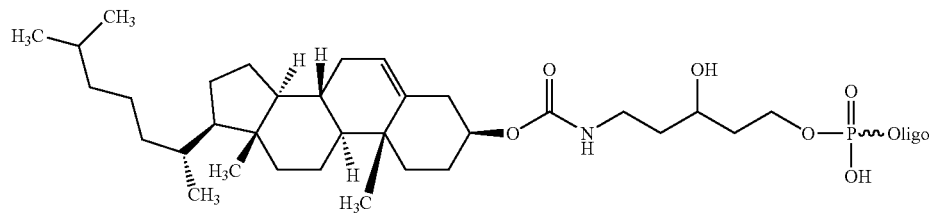

5. optionally a phosphate group at the 5' end of the antisense strand; and
6. optionally, a mismatch between at least one of nucleotides 1, 7, and 14 on the antisense strand (numbered from the 5' end) and the opposite nucleotide on the sense strand. The cholesterol molecule allows passive uptake of the mimic into cells.

The aforementioned methods of treating or preventing disease are carried out in an individual (e.g., a human patient) in need of such treatment or prevention. Pharmaceutical compositions suitable for such methods are disclosed herein. In addition, the modulation of the miRNA target genes of the disclosure (either an increase or decrease) can be carried out ex vivo e.g., using cells or tissue in vitro.

Identification of Cluster miRNAs that are Implicated in the Regulation of Apoptosis, c-Jun, and NF-κB in Breast Cancer Cells In one embodiment, cells are screened with cluster pools using HCS to detect phenotypes such as changes in viability (e.g. by performing cell counts) and changes in the degree of nuclear translocation of phospho-c-Jun and NF-κB. Changes in the translocation of c-Jun and NF-κB may be detected, for example, by quantitating the amount of c-Jun and NF-κB in the cytoplasm and in the nucleus (by immunofluorescence using anti-phospho-c-Jun and anti-NF-κB antibodies), and then comparing the results with appropriate controls.

NF-κB is composed of homo- and heterodimers of five members of the Rel family including NF-κB1 (p50), NF-κB2 (p52), RelA, RelB, and c-Rel (Rel). Activation of NF-κB is thought to be part of a stress response as it is activated by a variety of stimuli including growth factors, cytokines, lymphokines, UV, pharmacological agents, and stress. In its inactive form, NF-κB is sequestered in the cytoplasm, bound by members of the IκB family of inhibitor proteins, which include IκBα, IκBβ, IkBγ, and IkBε. The various stimuli that activate NF-κB cause phosphorylation of IκB (through the IκB kinase complex consisting of at least three proteins: IKK1/α, IKK2/β and IKK3/γ), which is followed by its ubiquitination and subsequent degradation. This results in the exposure of the nuclear localization signals (NLS) on NF-κB subunits and the subsequent translocation of the molecule to the nucleus. In the nucleus, NF-κB binds with the consensus sequence (5'GGGACTTTCC-3') (SEQ ID NO: 30) of various genes, activating their transcription. NF-κB activation is implicated in arthritis, asthma, heart disease, chronic inflammation, cancer and certain neuro-degenerative disorders.

c-Jun is activated through phosphorylation by c-Jun-N-terminal kinases (JNKs). Phosphorylated c-Jun family members then homodimerize to form a heterodimeric complex with c-Fos creating Activator Protein (AP) transcription factor, which migrates into the nucleus. AP-1 has been implicated in stress-induced apoptosis, heat shock, T-cell activation, cellular responses to inflammatory cytokines, and cellular transformation (Davis, R J. Biochem. Soc. Symp. 64:1-12), as well as ischemia/reperfusion (Morooka, H, et al. J. Biol. Chem. 270: 30084-30092). c-Jun is activated by a wide variety of stimuli, including anisomycin, epidermal growth factor, hydrogen peroxide, and TNF-alpha.

Example 1 below provides an example of a detailed protocol for a cluster pool screening method using MCF7 breast cancer cells in accordance with the disclosure. The phenotypes detected are object count per field (indicative of cell viability), increased c-Jun translocation, increased NF-κB translocation, and decreased NF-κB translocation.

Using the methods of the Example 1, it has been discovered that inhibition (for 48 hours) in MCF7 cells of the miRNA cluster which comprises miR-17-5p (caaagugcuuacagugcagguagu SEQ ID NO:1), miR-18a (uaaggugcaucuagugcagaua SEQ ID NO:2), miR-19a (ugugcaaaucuaugcaaaacuga SEQ ID NO:3), miR-20a (uaaagugcuuauagugcagguag SEQ ID NO:4), miR-19b (ugugcaaauccaugcaaaacuga SEQ ID NO:5), and miR-92 (uauugcacuuguccecggccug SEQ ID NO:6) (referred to herein as "the D6 cluster") leads to a decrease in cell number and an increase in NF-κB translocation and c-Jun translocation. All three of these phenotypes can be reproduced using an inhibitor of miR-17-5p alone at 50 nM (and possibly also at 8.3 nM). The results suggest that in breast cancer cells, inhibition of the D6 cluster, or inhibition of miR-17-5p alone, leads to apoptosis. Since apoptosis of breast cancer cells is a desirable result, this suggests that miR-17-5p inhibitors may be useful as therapeutic agents for the treatment of breast cancer. In addition, if the inhibition of miR-17-5p leads to apoptosis, then the overexpression of miR-17-5p may inhibit apoptosis in breast cancer cells. Accordingly, diagnostic or prognostic information may be obtained by assaying the level of miR-17-5p (or D6 cluster) expression, or by assaying the copy number of the D6 cluster, in breast tissue suspected of being cancerous or precancerous since relatively higher miR-17-5p expression would be expected to be correlated with a worse prognosis than relatively lower miR-17-5-p expression. In addition, identification of the target genes regulated by miR-17-5p will allow the design of additional diagnostic or prognostics assays (e.g by measuring mRNA levels for a target gene(s)), and will also allow the design of additional therapeutic agents e.g. small molecules that increase the level of expression of a miR-17-5p target or the activity of the gene product of a miR-17-5p target.

The seed region for miR-17-5p is shared by miR-20a, another member of the D6 cluster. However, inhibition of miR-20a is not able to generate the phenotypes observed when an inhibitor to miR-17-5p is used. This suggests that determinants outside of the seed region are important for target selection and also differs from the convention that the seed region alone (family members) determines miRNA target specificity.

Using the methods of Example 1, it has also been discovered that inhibition (for 48 hours) in MCF7 cells of the miRNA cluster which comprises miR-93 (aaagugcuguucgugcagguag SEQ ID NO:7), miR-106b (uaaagugcugacagugcagau SEQ ID NO:8), and miR-25 (cauugcacuugucucggucuga SEQ ID NO:9) (referred to herein as "the A3 cluster") leads to a decrease in cell number and an increase in NF-κB translocation and c-Jun translocation. All three of these phenotypes can be reproduced by an inhibitor of miR-106b alone (at 50 nM). The translocation of c-Jun and the translocation of NF-κB can be reproduced using the miR-93 inhibitor alone (at 50 nM). Because neither inhibitor can reproduce the phenotypes at the concentration it is present in the pool (17 nM), this suggests that there may be a synergistic effect or dosing effect between the inhibitors in the pool. Since apoptosis of breast cancer cells is a desirable result, this suggests that A3 cluster inhibitors may be useful as therapeutic agents for the treatment of breast cancer. In addition, because the inhibition of the A3 cluster leads to apoptosis, then the overexpression of the A3 cluster may inhibit apoptosis in breast cancer cells. Accordingly, diagnostic or prognostic information may be obtained by assaying the level of A3 cluster expression, or by assaying the copy number of the A3 cluster, in breast tissue suspected of being cancerous or precancerous. In addition, identification of the target genes regulated by the A3 cluster will allow the design of additional diagnostic or prognostics assays (e.g by measuring mRNA levels for a A3 cluster target gene(s)), and will also allow the design of additional therapeutic agents e.g. small molecules that increase the level of expression of an A3 cluster target or the activity of the gene product of an A3 cluster target.

Using the methods of Example 1, it has also been discovered that inhibition (for 48 hours) in MCF7 cells of the miRNA cluster which comprises miR-30e-5p (uguaaacauccuugacugga SEQ ID NO:10) and miR-30c (uguaaacauccuacacucucagc SEQ ID NO:11) cluster (referred to herein as "the C4 cluster") leads to an increase in c-Jun translocation. This phenotype can be reproduced by an inhibitor of miR-30e-5p alone at 50 nM and at 25 nM, suggesting that the phenotype observed for the pool of two inhibitors results entirely from the miR-30e-5p inhibitor.

Using the methods of Example 1, it has also been discovered that inhibition (for 48 hours) in MCF7 cells of the miRNA cluster which comprises miR-195 (uagcagcacagaaauauuggc SEQ ID NO:12) and miR-497 (cagcagcacacugugguuugu SEQ ID NO:13) (referred to herein as "the A5 cluster") leads to a decrease in NF-κB translocation. This phenotype can be reproduced by the miR-195 inhibitor alone at 50 nM, but not at 25 nM. This suggests that there may be a synergistic effect or dosing effect between the two inhibitors in the pool.

Using the methods of Example 1, it has also been discovered that inhibition (for 48 hours) in MCF7 cells of the miRNA cluster comprising miR-15a (uagcagcacauaauggu-uugug SEQ ID NO:14) and miR-16 (uagcagcacguaaauauug-gcg SEQ ID NO:15) (referred to herein as "the B3 cluster") results in a decrease in cell number. Since apoptosis of breast cancer cells is a desirable result, this suggests that B3 cluster inhibitors may be useful as therapeutic agents for the treatment of breast cancer. In addition, because the inhibition of the B3 cluster leads to apoptosis, then the overexpression of the B3 cluster may inhibit apoptosis in breast cancer cells. Accordingly, diagnostic or prognostic information may be obtained by assaying the level of B3 cluster expression, or by assaying the copy number of the B3 cluster, in breast tissue suspected of being cancerous or precancerous. In addition, identification of the target genes regulated by the B3 cluster will allow the design of additional diagnostic or prognostics assays (e.g by measuring mRNA levels for a B3 cluster target gene(s)), and will also allow the design of additional therapeutic agents e.g. small molecules that increase the level of expression of an B3 cluster target or the activity of the gene product of an B3 cluster target.

Using the methods of Example 1, it has also been discovered that inhibition (for 96 hours) in MCF7 cells of the miRNA cluster comprising miR-200b (uaauacugccug-guaaugauga SEQ ID NO:16), miR-200a (uaacacugucug-guaacgaugu SEQ ID NO:17), and miR-429 (uaauacugucug-guaaaccgu SEQ ID NO:18) (referred to herein as "the C5 cluster") results in a decrease in cell number and an increase in c-Jun translocation. Since apoptosis of breast cancer cells is a desirable result, this suggests that C5 cluster inhibitors may be useful as therapeutic agents for the treatment of breast cancer. In addition, because the inhibition of the C5 cluster leads to apoptosis, then the overexpression of the C5 cluster may inhibit apoptosis in breast cancer cells. Accordingly, diagnostic or prognostic information may be obtained by assaying the level of C5 cluster expression, or by assaying the copy number of the C5 cluster, in breast tissue suspected of being cancerous or precancerous. In addition, identification of the target genes regulated by the C5 cluster will allow the design of additional diagnostic or prognostics assays (e.g by measuring mRNA levels for a C5 cluster target gene(s)), and will also allow the design of additional therapeutic agents e.g. small molecules that increase the level of expression of an C5 cluster target or the activity of the gene product of an C5 cluster target.

Using the methods of Example 1, it has also been discovered that inhibition (for 96 hours) in MCF7 cells of the miRNA cluster comprising miR-30b (uguaaacauccuacacu-cagcu SEQ ID NO: 19) and miR-30d (uguaaacauccccgacug-gaag SEQ ID NO:20) (referred to herein as "the C2 cluster") results in a decrease in cell number and an increase in c-Jun translocation. Since apoptosis of breast cancer cells is a desirable result, this suggests that C2 cluster inhibitors may be useful as therapeutic agents for the treatment of breast cancer. In addition, because the inhibition of the C2 cluster leads to apoptosis, then the overexpression of the C2 cluster may inhibit apoptosis in breast cancer cells. Accordingly, diagnostic or prognostic information may be obtained by assaying the level of C2 cluster expression, or by assaying the copy number of the C2 cluster, in breast tissue suspected of being cancerous or precancerous. In addition, identification of the target genes regulated by the C2 cluster will allow the design of additional diagnostic or prognostics assays (e.g by measuring mRNA levels for a C2 cluster target gene(s)), and will also allow the design of additional therapeutic agents e.g. small molecules that increase the level of expression of an C2 cluster target or the activity of the gene product of an C2 cluster target.

Using the methods of Example 1, it has also been discovered that inhibition (for 96 hours) in MCF7 cells of the miRNA cluster comprising miR-141 (uaacacugucugguaaa-gaugg SEQ ID NO:21) and miR-200c (uaauacugc-cggguaaugaugga SEQ ID NO:22) (referred to herein as "the E3 cluster") results in a decrease in cell number and an increase in c-Jun translocation. Since apoptosis of breast cancer cells is a desirable result, this suggests that E3 cluster inhibitors may be useful as therapeutic agents for the treatment of breast cancer. In addition, because the inhibition of the E3 cluster leads to apoptosis, then the overexpression of the E3 cluster may inhibit apoptosis in breast cancer cells. Accordingly, diagnostic or prognostic information may be obtained by assaying the level of E3 cluster expression, or by assaying the copy number of the E3 cluster, in breast tissue suspected of being cancerous or precancerous. In addition, identification of the target genes regulated by the E3 cluster will allow the design of additional diagnostic or prognostics assays (e.g by measuring mRNA levels for a E3 cluster target gene(s)), and will also allow the design of additional therapeutic agents e.g. small molecules that increase the level of expression of an E3 cluster target or the activity of the gene product of an E3 cluster target.

Using the methods of Example 1, it has also been discovered that inhibition (for 96 hours) in MCF7 cells of the miRNA cluster comprising miR-502 (auccuugcuau-cugggugcua SEQ ID NO:23), miR-501 (aauccuuuguc-ccugggugaga SEQ ID NO:24), miR-500 (augcaccugggcaag-gauucug SEQ ID NO:25), miR-362 (aauccuuggaaccuaggugugagu SEQ ID NO: 26) and miR-188 (caucccuugcaugguggagggu SEQ ID NO:27) (referred to herein as "the E1 cluster") results in a decrease in cell number and an increase in c-Jun translocation. Since apoptosis of breast cancer cells is a desirable result, this suggests that E1 cluster inhibitors may be useful as therapeutic agents for the treatment of breast cancer. In addition, because the inhibition of the E1 cluster leads to apoptosis, then the overexpression of the E1 cluster may inhibit apoptosis in breast cancer cells. Accordingly, diagnostic or prognostic information may be obtained by assaying the level of E1 cluster expression, or by assaying the copy number of the E1 cluster, in breast tissue suspected of being cancerous or precancerous. In addition, identification of the target genes regulated by the E1 cluster will allow the design of additional diagnostic or prognostics assays (e.g by measuring mRNA levels for a E1 cluster target gene(s)), and will also allow the design of additional therapeutic agents e.g. small molecules that increase the level of expression of an E1 cluster target or the activity of the gene product of an E1 cluster target.

Using the methods of Example 1, it has also been discovered that inhibition (for 48 hours) in MCF7 cells of the miRNA cluster comprising miR-34b (caaucacuaacuccacugccau SEQ ID NO:28) and miR-34c (aggcaguguaguuagcugauugc SEQ ID NO:29) (referred to herein as "the B2 cluster") results in a decrease in cell number and an increase in c-Jun translocation. Since apoptosis of breast cancer cells is a desirable result, this suggests that B2 cluster inhibitors may be useful as therapeutic agents for the treatment of breast cancer. In addition, because the inhibition of the B2 cluster leads to apoptosis, then the overexpression of the B2 cluster may inhibit apoptosis in breast cancer cells. Accordingly, diagnostic or prognostic information may be obtained by assaying the level of B2 cluster expression, or by assaying the copy number of the B2 cluster, in breast tissue suspected of being cancerous or precancerous. In addition, identification of the target genes regulated by the B2 cluster will allow the design of additional diagnostic or prognostics assays (e.g by measuring mRNA levels for a B2 cluster target gene(s)), and will also allow the design of additional therapeutic agents e.g. small molecules that increase the level of expression of an B2 cluster target or the activity of the gene product of an B2 cluster target.

The following examples are non-limiting.

EXAMPLES

Example 1

Screening of MCF7 Cells with miRNA Cluster Pools for Changes in Cell Viability, c-Jun Translocation, and NF-κB Translocation The following reagents were used in a cluster pool screen using MCF7 breast cancer cells:
Reagents
Fixative—pre-warmed 3.7% formaldehyde
Wash buffer—PBS
Detergent—Cellomics Detergent Buffer (0.1% Tween 20)
Permeabilization Buffer—Cellomics Permeabilization Buffer (0.5% TritonX-100)
Blocking Buffer—Cellomics Blocking Reagent (1% serum)
Primary Antibodies (per plate)
5.5 ml Blocking Buffer
55 ul—c-Jun (20 ug/ml)
55 ul—NF-κB (20 ug/ml)
Secondary Antibodies/Stain (per plate)
5.5 ml Blocking Buffer
55 ul 0.1 mg/ml Hoechst (stock 10 mg/ml, 100 ng/ml final)
55 ul Alexa 488 Goat anti-mouse (20 ug/ml)
27.5 ul Alexa 647 Goat anti-rabbit (10 ug/ml)
27.5 ul Rhodamine Phalloidin (300 U stock)

Figure 2:
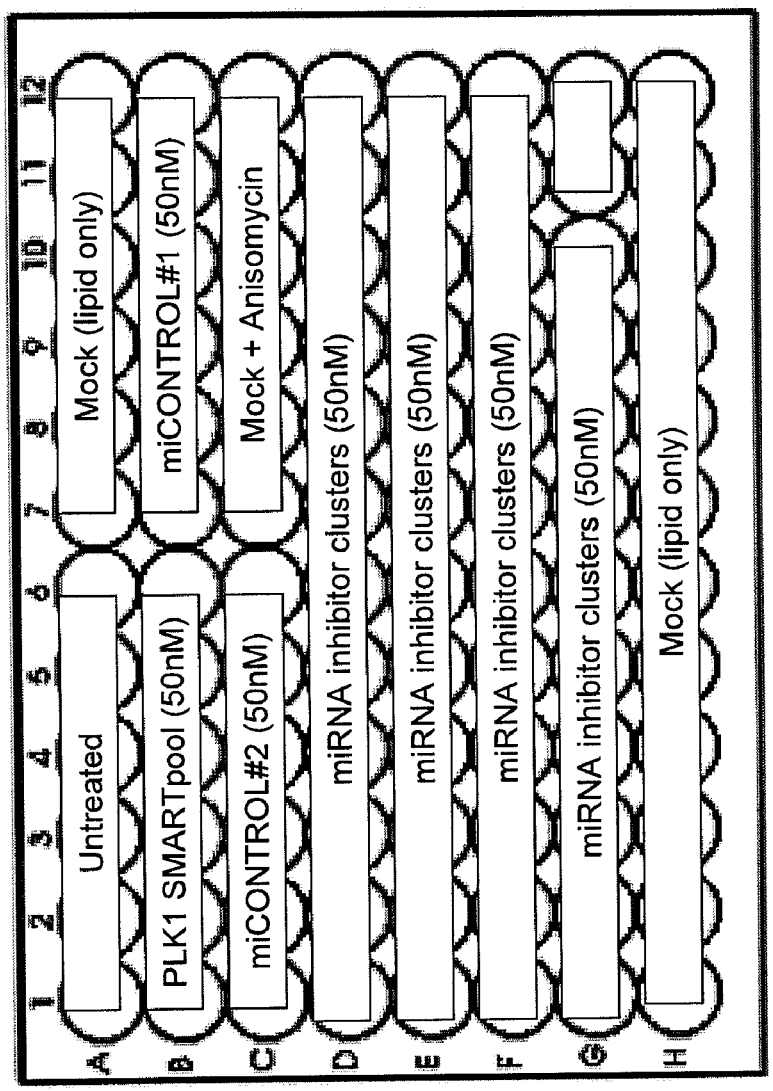
FIG. 2 illustrates schematically the layout of a multiwell plate used in a HCS-based cluster pool screen according to the disclosure.

The following protocol was used to initially screen each of the 46 cluster pools (one cluster pool for each miRNA cluster) for changes in c-Jun and NF-κB translocation and for changes in cell viability (measured as object count per field):

1. Performed transfections using each of 46 cluster pools (total RNA concentration per cluster pool=50 nM)
2. Incubated ~48 hours
3. Cells fixed with pre-warmed 3.7% Formaldehyde
4. Incubated at room temperature for 15-30 minutes.
5. Plates washed with PBS, sealed and stained (described below) or stored at 4 degrees until ready for staining
6. Plates aspirated and washed with 100 ul PBS
7. Aspirated and added 100 ul/well of Permeabilization Buffer
8. Incubated at RT for 90 seconds
9. Aspirated and washed 2× with 100 ul/well PBS
10. Aspirated and added 50 ul/well of primary antibody solution
11. Incubated at RT for 1 hour
12. Aspirated and added 100 ul of Detergent Buffer
13. Incubated at RT for 15 minutes
14. Aspirated and washed 3× with 100 ul of PBS
15. Aspirated and added 50 ul of secondary staining solution
16. Incubated at RT for 1 hour
17. Aspirated and added 100 ul of Detergent Buffer
18. Incubated at RT for 15 minutes
19. Aspirated and washed 3× with 100 ul of PBS
20. Aspirate and added with 200 ul of PBS
21. Plates sealed and run on the ArrayScan The following controls were also included on each assay plate: untreated cells; mock transfected cells (i.e., cells treated with transfection reagents only); cells treated with PLK1 siRNAs (PLK1 Smartpool, available from Dharmacon); cells treated with miRNA inhibitor controls (miCONTROL 1 and 2, available from Dharmacon, which are based on C. elegans miRNAs that have beenBLASTed against all human, mouse, and rat genomic sequences and miRNA sequences in the miRBase Sequence Database and have no known target in MCF7 cells); and cells treated with transfection reagents plus anisomycin (an activator of c-Jun). The PLK1 siRNAs and anisomycin both induce apoptosis and serve as positive controls. The assays were performed in triplicate using three plates. Each plate contained a complete set of assays and controls. A schematic of an assay plate is provided in FIG. 2.

Initial Screening and Identification of Potential Hits

Figure 3:
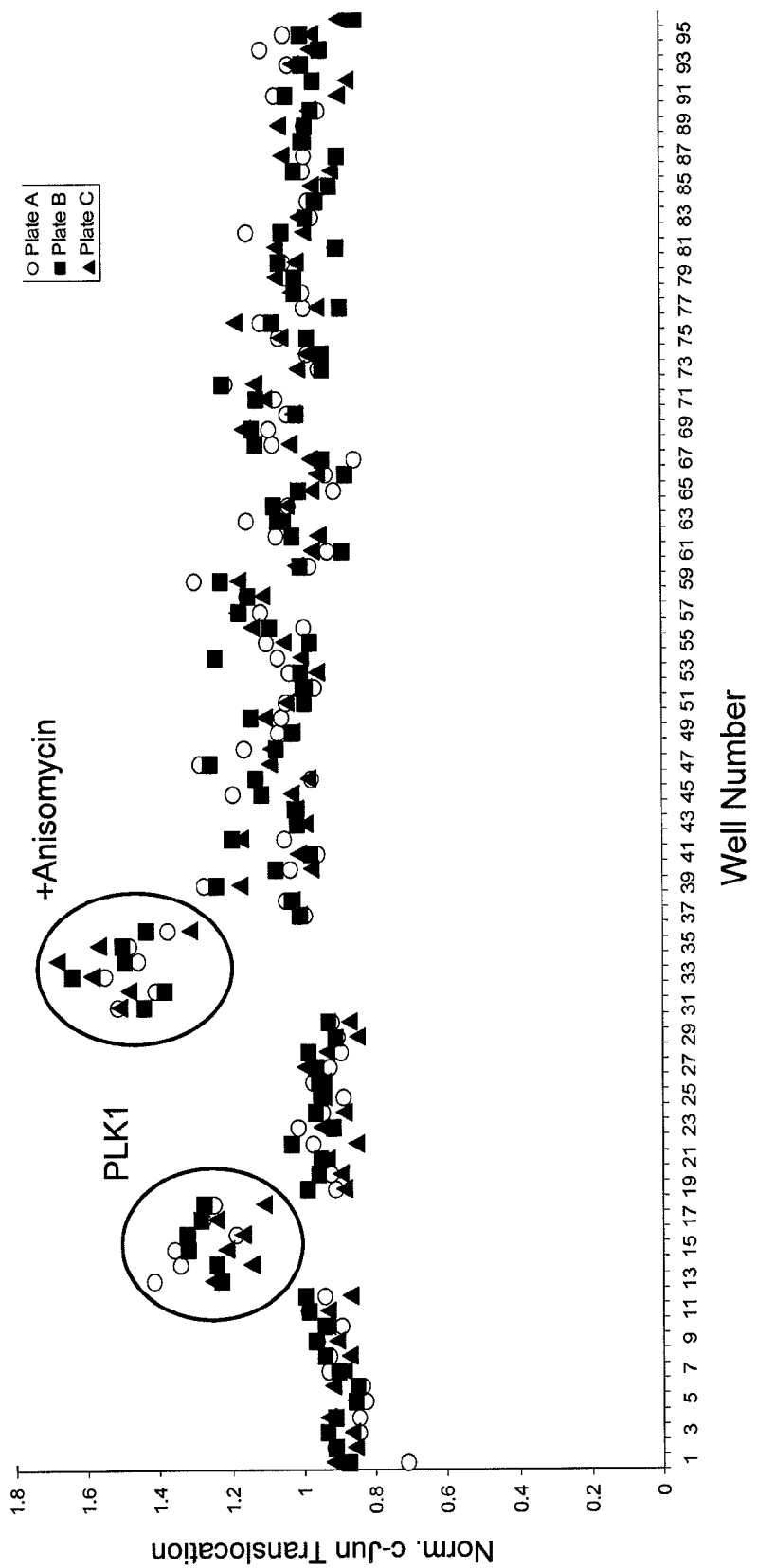
FIG. 3 provides a graph showing normalized data for c-Jun translocation in a 96 well multiwell plate HCS-based cluster pool screen. Each point represents a well in the 96 well plate (the X axis indicates the well number) and the different shapes represent the triplicate plates (circles are plate A wells; squares are plate B wells, and triangles are plate C wells). The Y axis provides the difference in nuclear and cytoplasmic staining of c-Jun (normalized). The positive controls, PLK1 siRNA and anisomycin treatment, are indicated by the large circles.

Following incubation for 48 hours after transfection with cluster pools, plates were fixed, stained, and analyzed on the ArrayScan VTi. Data were plate normalized by dividing values by the median of the plate. FIG. 3 shows a plate normalized data for c-Jun translocation which measures the difference in nuclear and cytoplasmic staining of c-Jun. Each point represents a well in the 96 well plate and the different shapes represent the triplicate plates. Both positive controls (circled), PLK1 siRNA and anisomycin treatment, result in an increase in activated c-Jun (more c-Jun staining in the nucleus). c-Jun translocation is a fairly "clean" assay and has minimal scatter. Z' factors were calculated based on PLK1 and the two negative controls (miControl 1 and 2) for each of the plates and were as follows: replicate A=0.02; replicate B=0.31; replicate C=−0.11.

Figure 4:
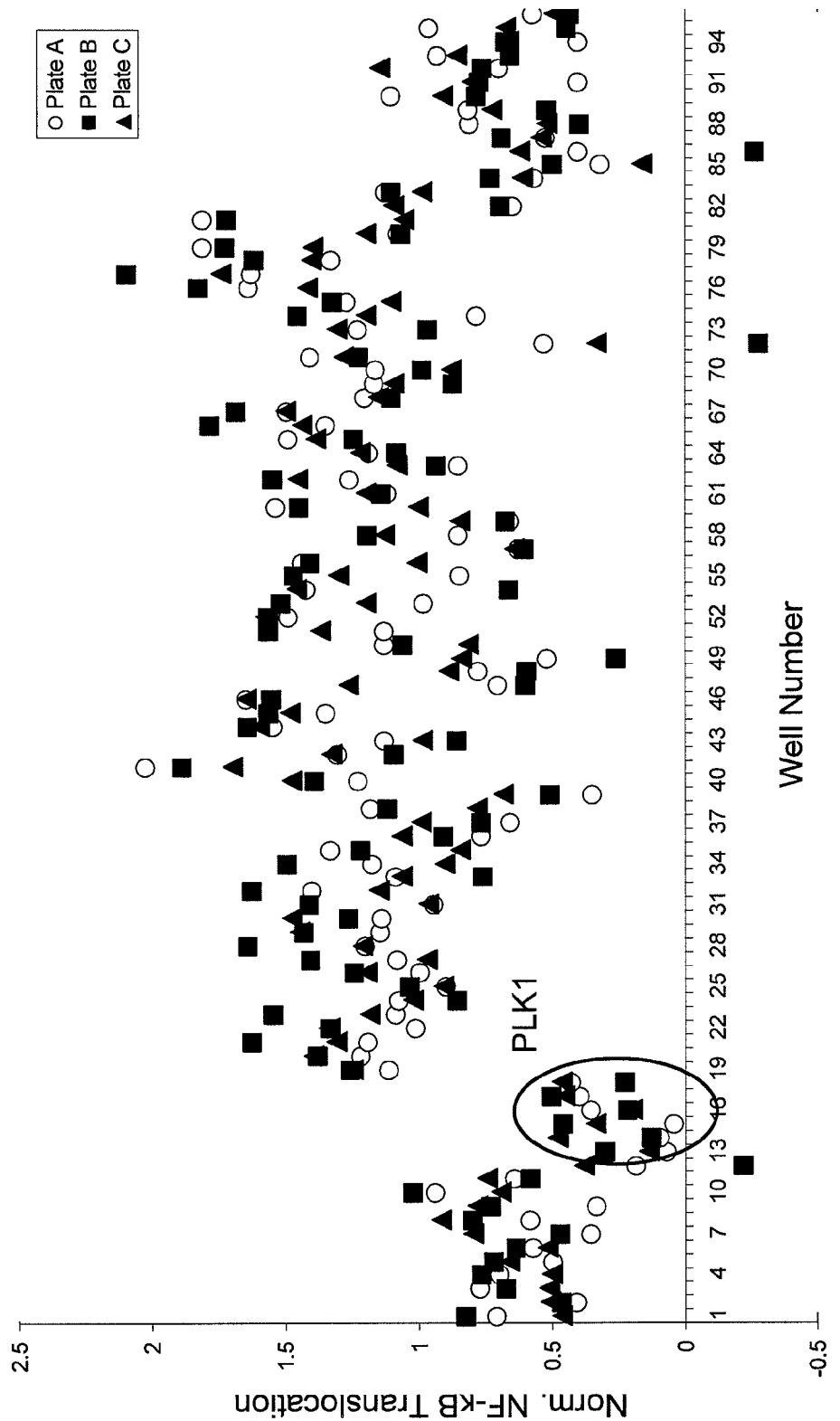
FIG. 4 provides a graph showing normalized data for NF-κB translocation in a 96 well multiwell plate HCS-based cluster pool screen (the same screen as in FIG. 3). Each point represents a well in the 96 well plate (the X axis provides the well number) and the different shapes represent the triplicate plates (circles are plate A wells; squares are plate B wells, and triangles are plate C wells). The Y axis indicates the difference in nuclear and cytoplasmic staining of NF-κB (normalized). The PLK1 siRNA is the positive control (circled).

FIG. 4 shows plate normalized data for NF-κB translocation (which measures the difference in nuclear and cytoplasmic staining of NF-κB) for the same plate as in FIG. 3. Each point represents a well in the 96 well plate and the different shapes represent the triplicate plates. The PLK1 siRNA is the positive control (circled). The NF-κB translocation assay is a "less clean" assay with more scatter. The Z' factors associated with this assay are: replicate A=0.04; replicate B=−0.12; replicate C=−0.12. It is important to remember that this is the same plate, same transfection, same cells that were analyzed in the previous c-Jun assay, so the lower z' factors are due only to this specific NF-κB assay, not the experiment itself.

Figure 5:
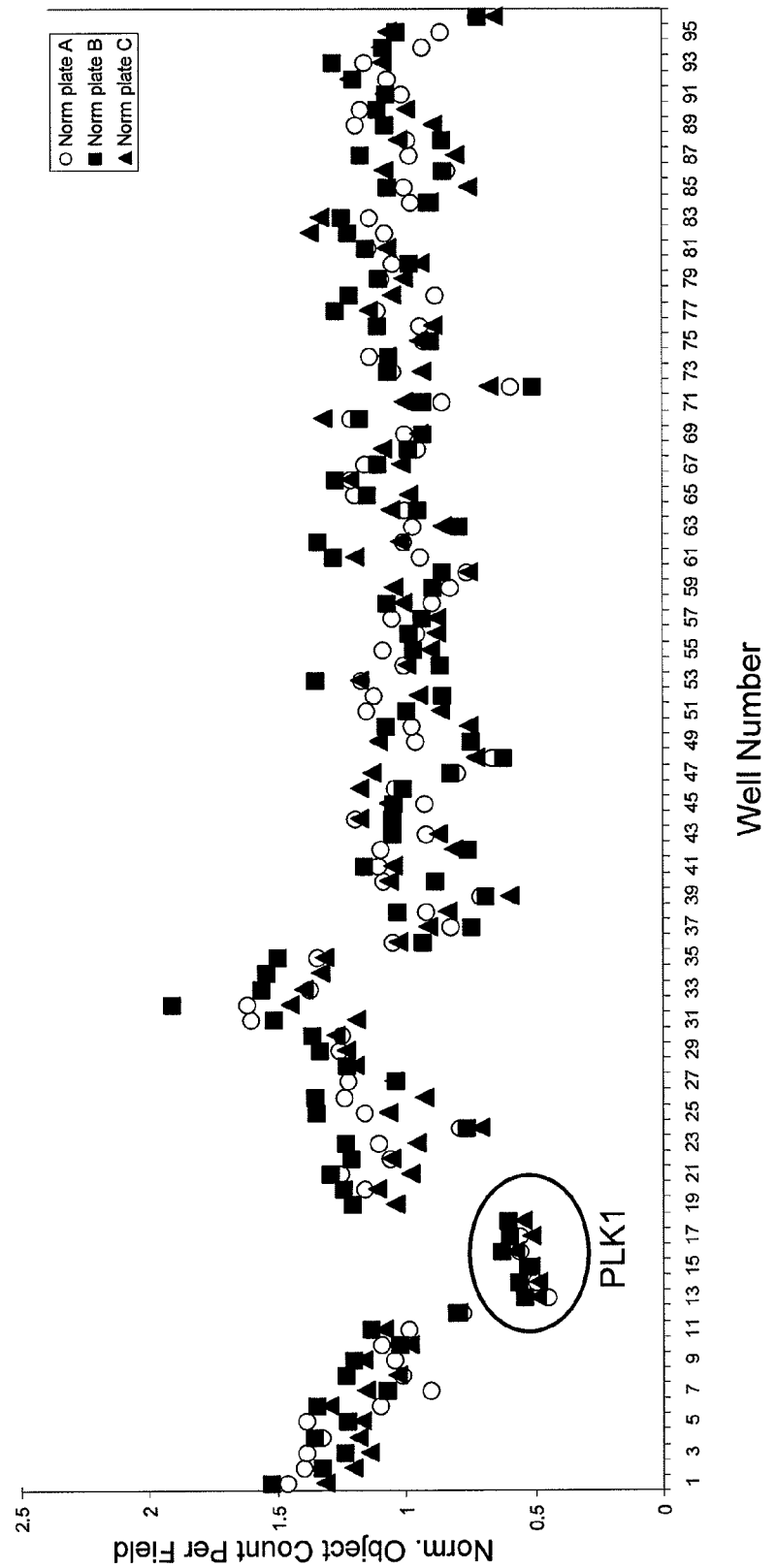
FIG. 5 provides a graph showing normalized data for object count per field (Y axis), which is an indication of viability, in a 96 well multiwell plate HCS-based cluster pool screen (the same screen as in FIGS. 3 and 4). Each point represents a well in the 96 well plate (the X axis provides the well number) and the different shapes represent the triplicate plates (circles are plate A wells; squares are plate B wells, and triangles are plate C wells). The PLK1 siRNA is the positive control (circled).

FIG. 5 shows plate normalized data for object count per field which is an indication of viability. Each point represents a well in the 96 well plate and the different shapes represent the triplicate plates. The PLK1 siRNA is the positive control (circled) and results in a decrease in cells per field. The z' factors for this assay are: replicate A=0.08; replicate B=0.00; replicate C=−0.04.

Robust Z scores were calculated for object count per field for each replicate. Potential hits were identified as having a robust Z score ≦2.5 (decreased object count per field) for at least 2 of the 3 replicates (see Table 1 which indicates the Z scores for the corresponding clusters). Three of the 4 potential hits had significant robust Z scores in all three replicates while one of them (inhibition of the C5 cluster (miR-200b, 200a, 429); well E12) had one replicate (replicate B) that did not have a significantly reduced robust Z score.

Rescreening of Potential Hits

Figure 6:
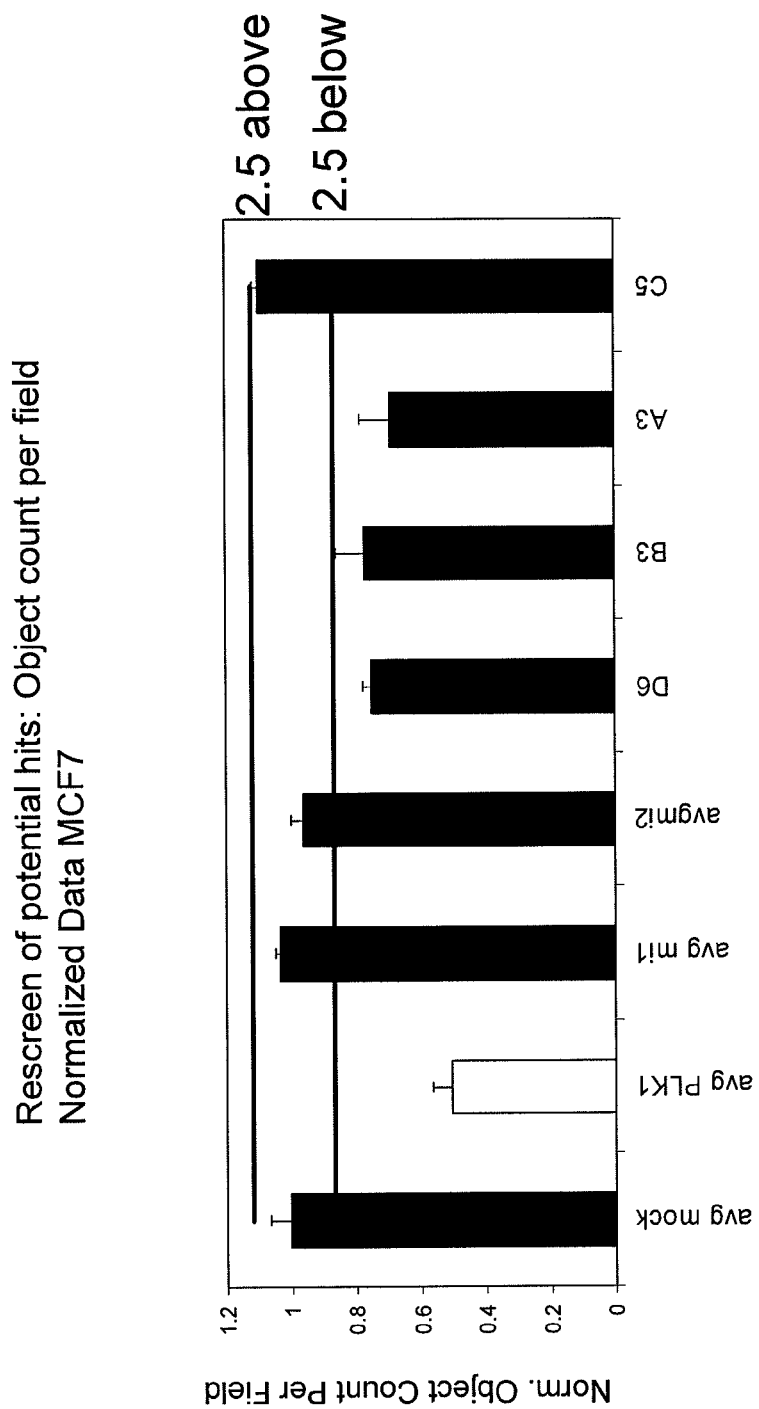
FIG. 6 shows the normalized data from the re-screening of the 4 potential hits in the object count per field phenotype. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

The potential inhibitor cluster hits identified in Tables 1-3 were rescreened using the same methodology. FIG. 6 shows the normalized data from the re-screening of the 4 potential hits in the object count per field phenotype. PLK1 served as the positive control, and miControl 1 and 2 (mi1, mi2) served as the negative controls. The horizontal black lines indicate the values for 2.5 standard deviations above and below, respectively, the average of the negative controls. As shown in Table 4, 3 of the 4 potential hits (inhibition of the D6, B3, and A3 clusters) were confirmed as hits while one (inhibition of the C5 cluster) was not. Interestingly, the one that was not confirmed was the one that had only 2/3 replicates with significant robust z score.

TABLE 1

| Well | Replicate A | Replicate B | Replicate C | Inhibitor cluster |
|---|---|---|---|---|
| F12 | −4.7 | −4.3 | −3.2 | (D6) miR-17-5p, 18a, 19a, 20a, 19b, 92 |
| D12 | −3.8 | −3.3 | −2.78 | (B3) miR-16, 15a |
| D3 | −3.3 | −2.7 | −4.0 | (A3) miR-93, 106b, 25 |
| E12 | −2.7 | −1.3 | −2.5 | (C5) miR-200b, 200a, 429 |

Robust Z scores were calculated for c-Jun translocation phenotype for each replicate. Potential hits were identified as having a robust Z score ≧2.5 (increase in activated c-Jun) for at least 2 of the 3 replicates (see Table 2 which indicates the Z scores for the corresponding clusters). Two of the 6 potential hits had significant robust Z scores in all three replicates (inhibition of the C4 cluster (miR030e-5p, 30c) and inhibition of the A3 cluster (miR-93, 106b, 25)) while four of them had one replicate that did not have a significantly reduced robust Z score.

TABLE 2

| Well | Replicate A | Replicate B | Replicate C | Inhibitor cluster |
|---|---|---|---|---|
| E11 | 4.7 | 3.7 | 3.4 | (C4) miR-30e-5p, 30c |
| D11 | 4.5 | 4.4 | 1.4 | (B2) miR-34b, 34c |
| D3 | 4.3 | 4.0 | 3.4 | (A3) miR-93, 106b, 25 |
| F12 | 3.1 | 3.6 | 2.3 | (D6) miR-17-5p, 18a, 19a, 20a, 19b, 92 |
| D6 | 0.1 | 3.2 | 3.3 | (A6) miR-132, 212 |
| E9 | 1.3 | 2.8 | 3.5 | (C2) miR-30b, 30d |

Robust Z scores were calculated for the NF-κB translocation phenotype for each replicate. In the screen, potential hits were obtained that had both an increase in NF-κB activation and a decrease in NF-κB nuclear translocation. Because the NF-κB assay is a noisier assay, the stringency of the cutoff for potential hits was decreased. Potential hits were identified as having a robust Z score ≧2.0 (increase in activated NF-κB) or ≦2.0 (decrease in nuclear translocation) for at least 2 of the 3 replicates (see Table 3 which indicates the Z scores for the corresponding inhibitor clusters).

TABLE 3

| Well | Replicate A | Replicate B | Replicate C | Inhibitor cluster | |
|---|---|---|---|---|---|
| D5 | −2.8 | −2.0 | −2.4 | (A5) miR-195, 497 | Decrease in nuclear translocation |
| G5 | −1.5 | −2.6 | −2.7 | (E1) miR-502, 501, 500, 362, 188 | |
| D3 | 2.9 | 2.0 | 2.5 | (A3) miR-93, 106b, 25 | Increase in nuclear translocation |
| E1 | 2.3 | 2.7 | 1.8 | (B4) miR-99a, let7c | |
| F12 | 2.2 | 4.3 | 4.2 | (D6) miR-17-5p, 18a, 19a, 20a, 19b, 92 | |

TABLE 4

| Replicate A | Replicate B | Replicate C | Inhibitor cluster |
|---|---|---|---|
| −4.7 | −4.3 | −3.2 | (D6) miR-17-5p, 18a, 19a, 20a, 19b, 92 |
| −3.8 | −3.3 | −2.78 | (B3) miR-16, 15a |
| −3.3 | −2.7 | −4.0 | (A3) miR-93, 106b, 25 |
| −2.7 | −1.3 | −2.5 | (C5) miR-200b, 200a, 429 |

Figure 7:
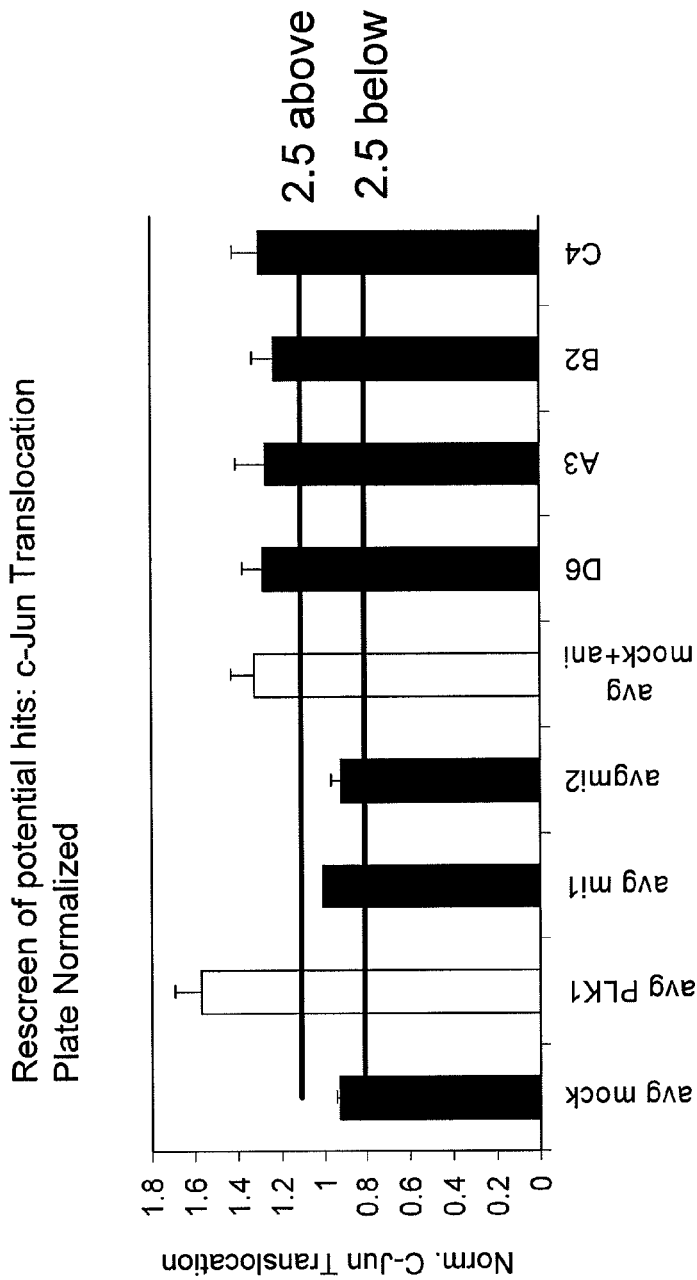
FIG. 7 shows normalized data from the re-screening of 4 potential hits in the activated c-Jun phenotype. PLK1 served as the positive control ("avg PLK1") as does anisomycin treatment ("avg mock+ani"), and miControl 1 and 2 ("avg mi1", "avg mi2") served as the negative controls. The horizontal black lines indicate the values for 2.5 standard deviations above and below, respectively, the average of the negative controls.

FIG. 7 shows normalized data from the re-screening of 4 potential hits in the activated c-Jun phenotype. PLK1 served as the positive control as does anisomycin treatment, and miControl 1 and 2 (mi1, mi2) served as the negative controls. The horizontal black lines indicate the values for 2.5 standard deviations above and below, respectively, the average of the negative controls. As shown in Table 5, all of the 4 potential hits (inhibition of the D6, A3, B2, and C4 clusters) tested in this re-screen were confirmed.

TABLE 5

| Replicate A | Replicate B | Replicate C | Inhibitor cluster |
|---|---|---|---|
| 3.1 | 3.6 | 2.3 | (D6) miR-17-5p, 18a, 19a, 20a, 19b, 92 |
| 4.3 | 4.0 | 3.4 | (A3) miR-93, 106b, 25 |
| 4.5 | 4.4 | 1.4 | (B2) miR-34b, 34c |
| 4.7 | 3.7 | 3.4 | (C4) miR-30e-5p, 30c |

Figure 8:
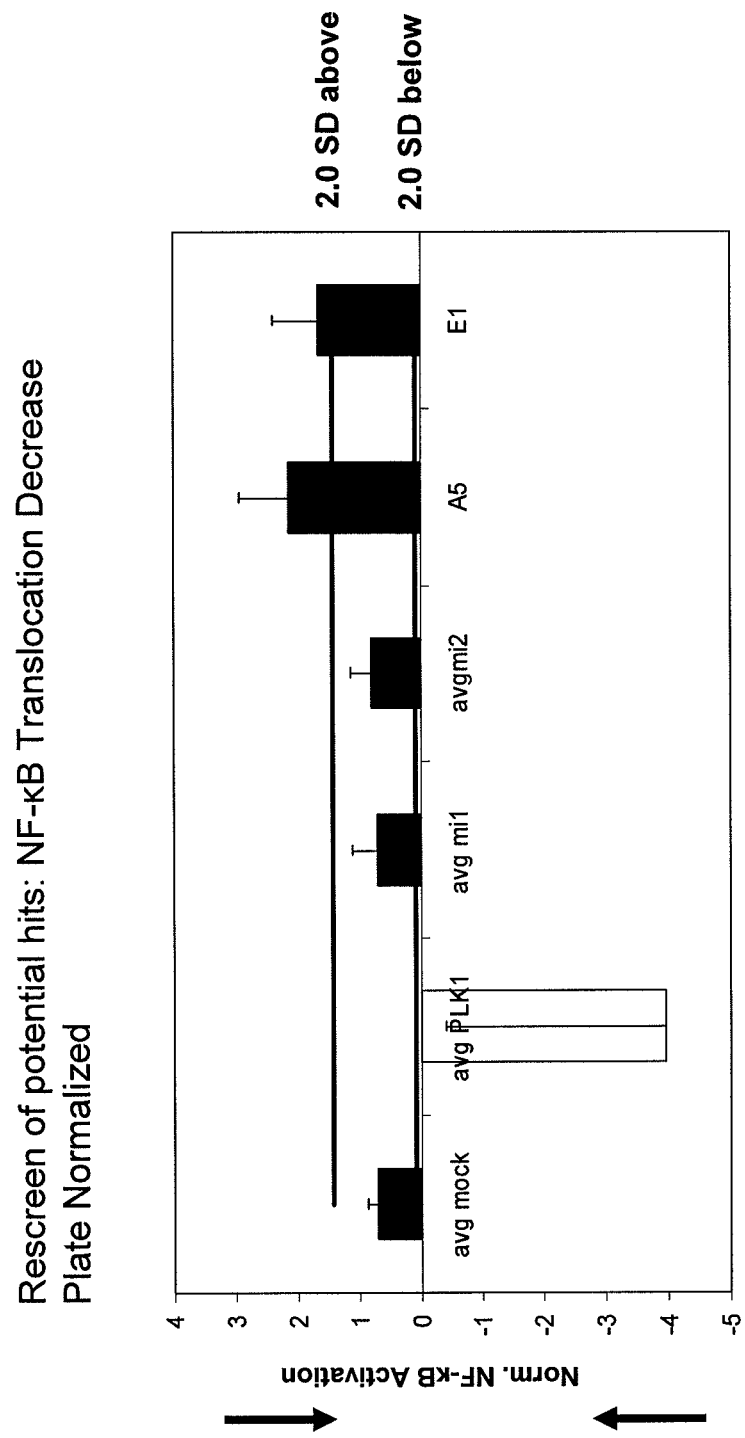
FIG. 8 shows the normalized data from the re-screening of the potential hits that had a decrease in nuclear translocated NF-κB. Negative values represent an increase in activation while the positive numbers represent a decrease in activation. PLK1 ("avg PLK1") results in an increase in NF-κB translocation, and miControl 1 and 2 ("avg mi1", "avg mi2") served as the negative controls. The horizontal black lines indicate the values for 2.0 standard deviations above and below, respectively, the average of the negative controls.

FIG. 8 shows the normalized data from the re-screening of the potential hits that had a decrease in nuclear translocated NF-κB. The arrows to the left of the graph indicate that the negative values represent an increase in activation while the positive numbers represent a decrease in activation. PLK1 results in an increase in NF-κB translocation, and miControl 1 and 2 (mi1, mi2) served as the negative controls. The horizontal black lines indicate the values for 2.0 standard deviations above and below, respectively, the average of the negative controls. Table 6 shows that both potential hits (inhibition of the A5 and E1 clusters) tested in this re-screen were confirmed.

TABLE 6

| Replicate A | Replicate B | Replicate C | Inhibitor cluster |
|---|---|---|---|
| −2.8 | −2.0 | −2.4 | (A5) miR-195, 497 |
| −1.5 | −2.6 | −2.7 | (E1) miR-502, 501, 500, 362, 188 |

Figure 9:
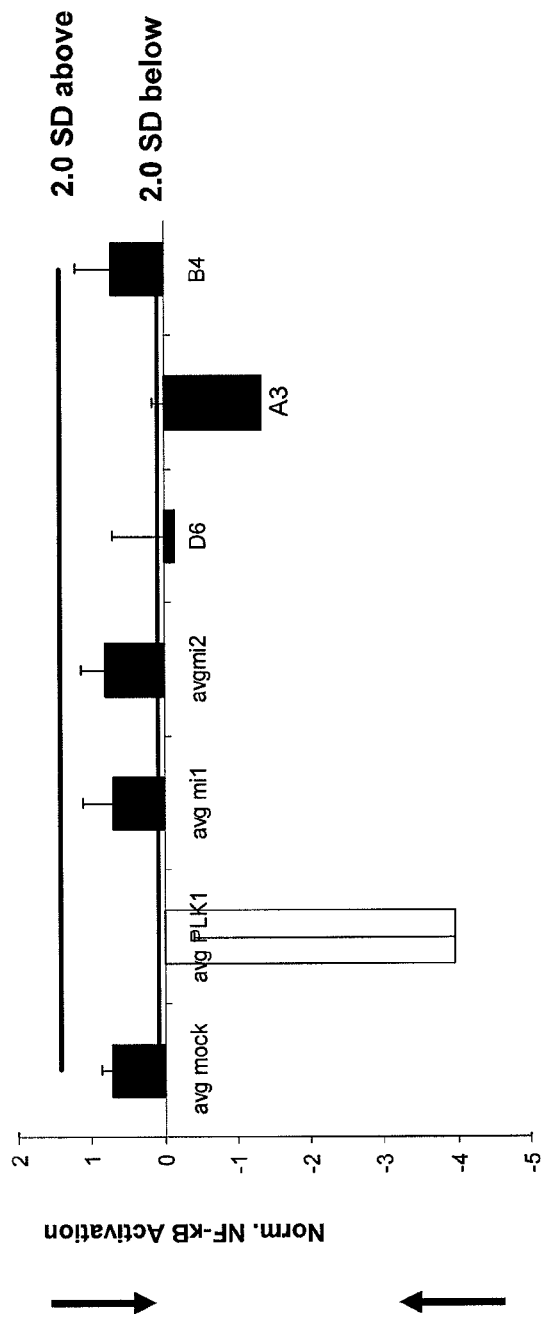
FIG. 9 shows the normalized data from the re-screening of the potential hits that had an increase in nuclear translocated NF-κB. Negative values represent an increase in activation while the positive numbers represent a decrease in activation. PLK1 ("avg PLK1") results in an increase in NF-κB translocation, and miControl 1 and 2 ("avg mi1", "avg mi2") served as the negative controls. The horizontal black lines indicate the values for 2.0 standard deviations above and below, respectively, the average of the negative controls.

FIG. 9 shows the normalized data from the re-screening of the potential hits that had an increase in nuclear translocated NF-κB. The arrows to the left of the graph indicate that the negative values represent an increase in activation while the positive numbers represent a decrease in activation. PLK1 results in an increase in NF-κB translocation, and miControl 1 and 2 (mi1, mi2) served as the negative controls. The horizontal black lines indicate the values for 2.0 standard deviations above and below, respectively, the average of the negative controls. Table 7 shows that 2 of the 3 potential hits (inhibition of the D6 and A3 clusters) tested in this re-screen were confirmed.

TABLE 7

| Replicate A | Replicate B | Replicate C | Inhibitor cluster |
|---|---|---|---|
| 2.2 | 4.3 | 4.2 | (D6) miR-17-5p, 18a, 19a, 20a, 19b, 92 |
| 2.9 | 2.0 | 2.5 | (A3) miR-93, 106b, 25 |
| 2.3 | 2.7 | 1.8 | (B4) miR-99a, let7c |

Dose Response and Timepoint Screening

The confirmed hits from the rescreening process were then further screened at different doses to determine whether there were concentration dependent effects for the cluster pools. In addition, screening was performed at 96 hours post-transfection to determine whether effects may be more pronounced at later timepoints.

Figure 10:
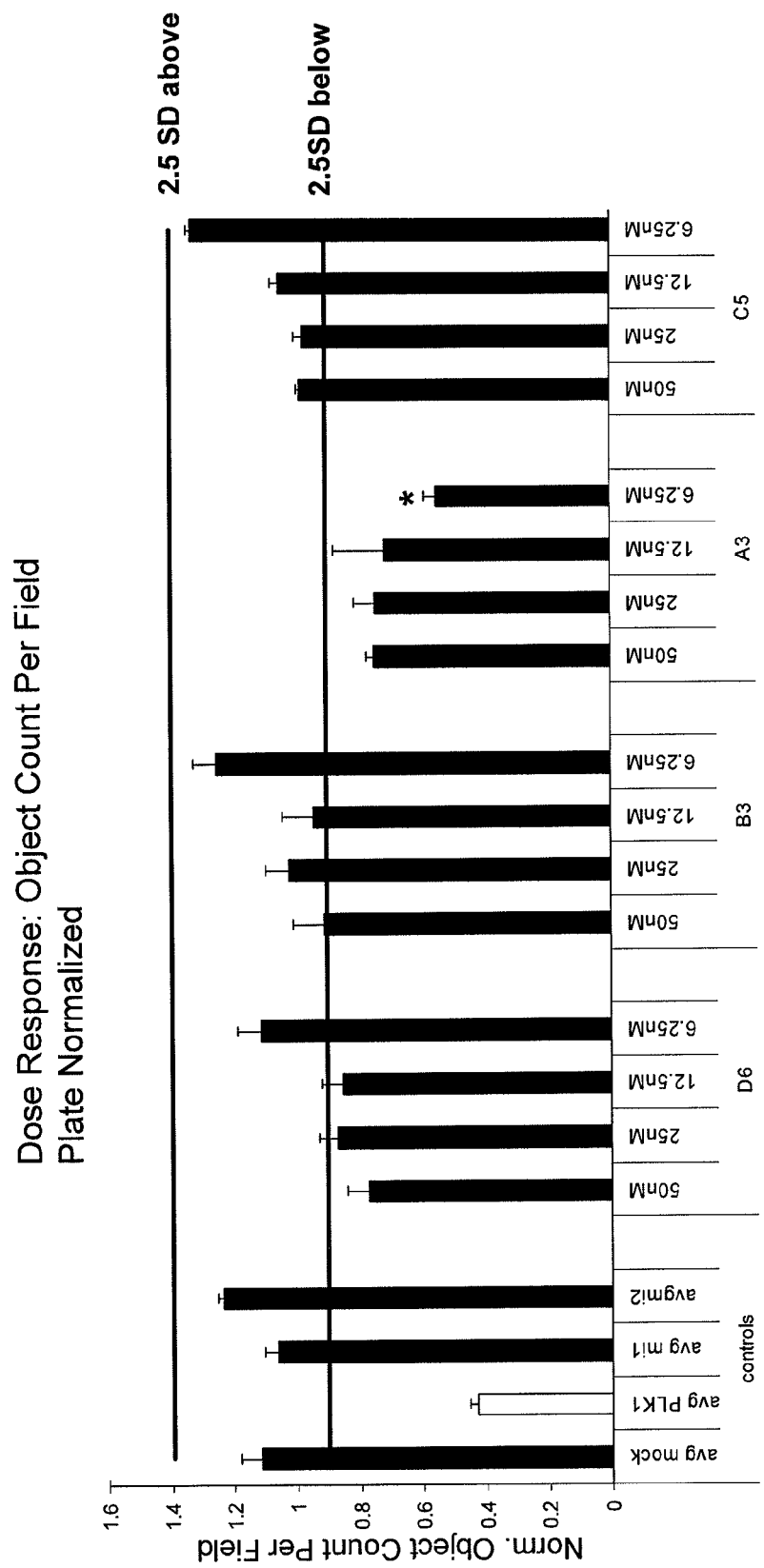
FIG. 10 shows normalized data from the dose response curve of the 4 potential hits in the object count per field phenotype at 48 hrs. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls. The asterisk indicates a data point that is an outlier and is therefore not significant.

FIG. 10 shows normalized data from the dose response curve of the 4 potential hits in the object count per field phenotype at 48 hrs. PLK1 served as the positive control, and miControl 1 and 2 (mi1, mi2) served as the negative controls. The horizontal black lines indicate the values for 2.5 standard deviations above and below, respectively, the average of the negative controls. 3 of the 4 potential hits confirm the decreased object count per field (inhibition of the B3 cluster is borderline) and inhibition of the C5 cluster did not confirm (same result as the re-screen). In terms of dose response, there is slight but not dramatic dose response associated with inhibition of the D6 cluster, but there is no dose response associated with inhibition of the A3 cluster. This suggests that perhaps inhibition of the A3 cluster is more potent. Inhibition of the C5 cluster appears to be dose responsive suggesting there may be a phenotypic effect of C5 but it is not as statistically significant. This dose curve was a 2-fold dose which may not produce a dramatic dose response. The asterisk indicates an experimental outlier.

Figure 11:
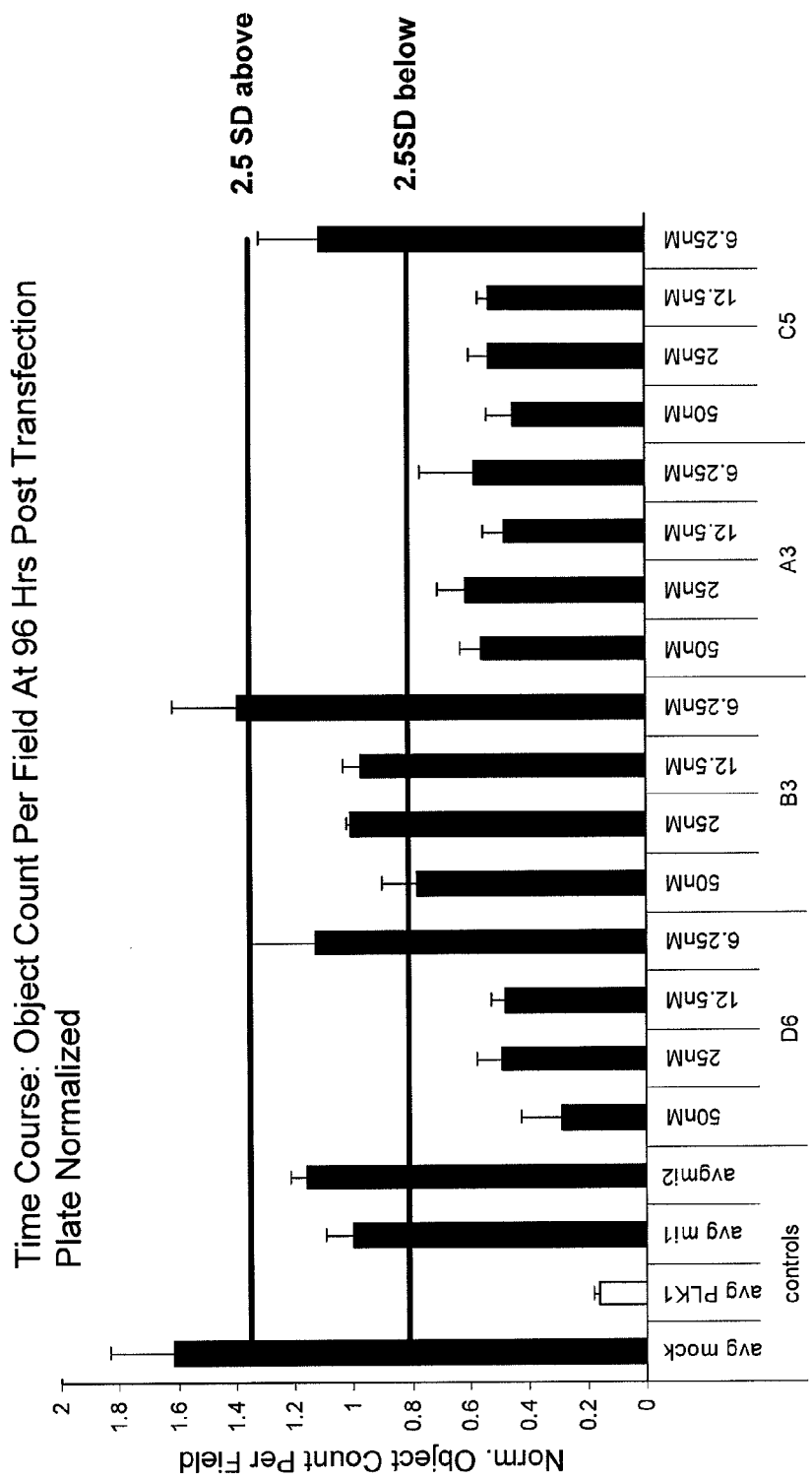
FIG. 11 shows normalized data from the dose response curve of the 4 potential hits in the object count per field phenotype at 96 hrs. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

FIG. 11 shows normalized data from the dose response curve of the 4 potential hits in the object count per field phenotype at 96 hrs. PLK1 served as the positive control, and miControl 1 and 2 (mi1, mi2) served as the negative controls. The horizontal black lines indicate the values for 2.5 standard deviations above and below, respectively, the average of the negative controls. At 96 hrs, there is a more dramatic dose response for inhibition of the D6 cluster and inhibition of the B3 cluster. Inhibition of the A3 cluster does not exhibit a dose response at 96 hrs either. Inhibition of the C5 cluster at 96 hrs is now having a significant effect.

Figure 12A:
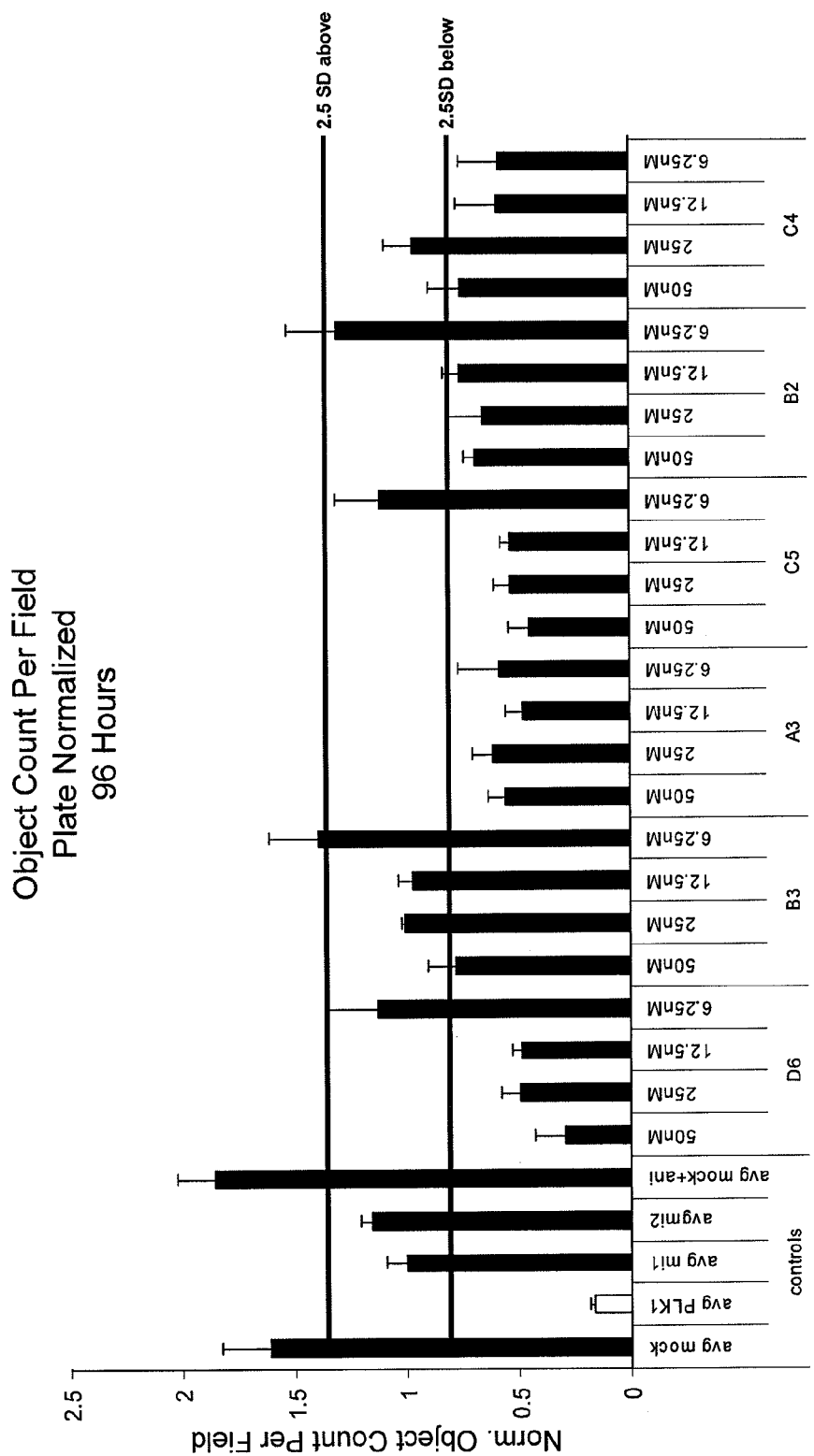
FIGS. 12A-12B show normalized data from the dose response curve of other clusters in the object count per field phenotype at 96 hrs that were not initially picked up as hits in the original screen. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.
Figure 12B:
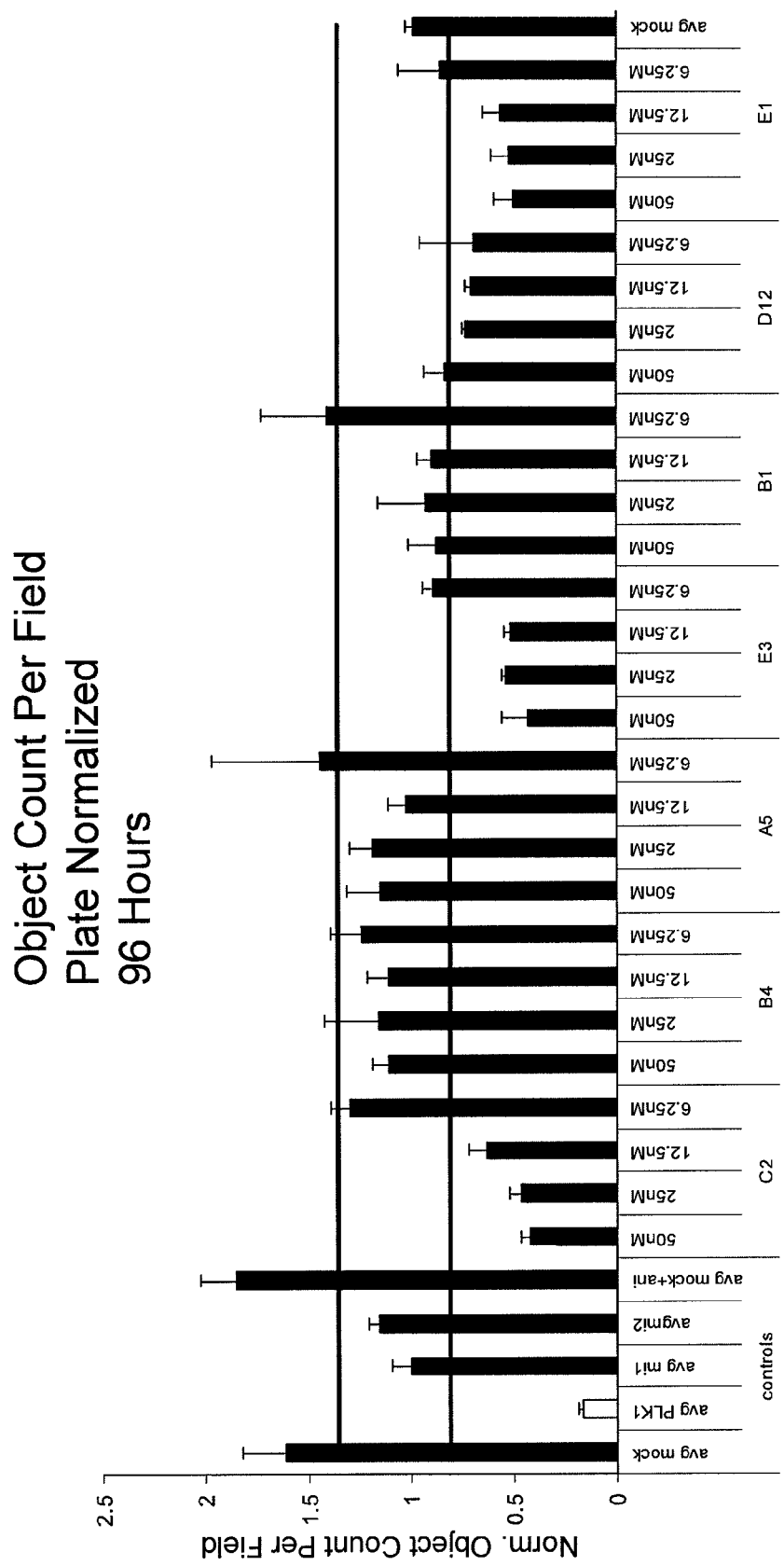

FIGS. 12A-12B show normalized data from the dose response curve of other clusters in the object count per field phenotype at 96 hrs that were not initially picked up as hits in the original screen. PLK1 served as the positive control, and miControl 1 and 2 (mi1, mi2) served as the negative controls. The horizontal black lines indicate the values for 2.5 standard deviations above and below, respectively, the average of the negative controls. At 96 hrs, some clusters have an increased response and effect on object count per field, suggesting there are delayed downstream effects of these inhibitors.

Figure 13:
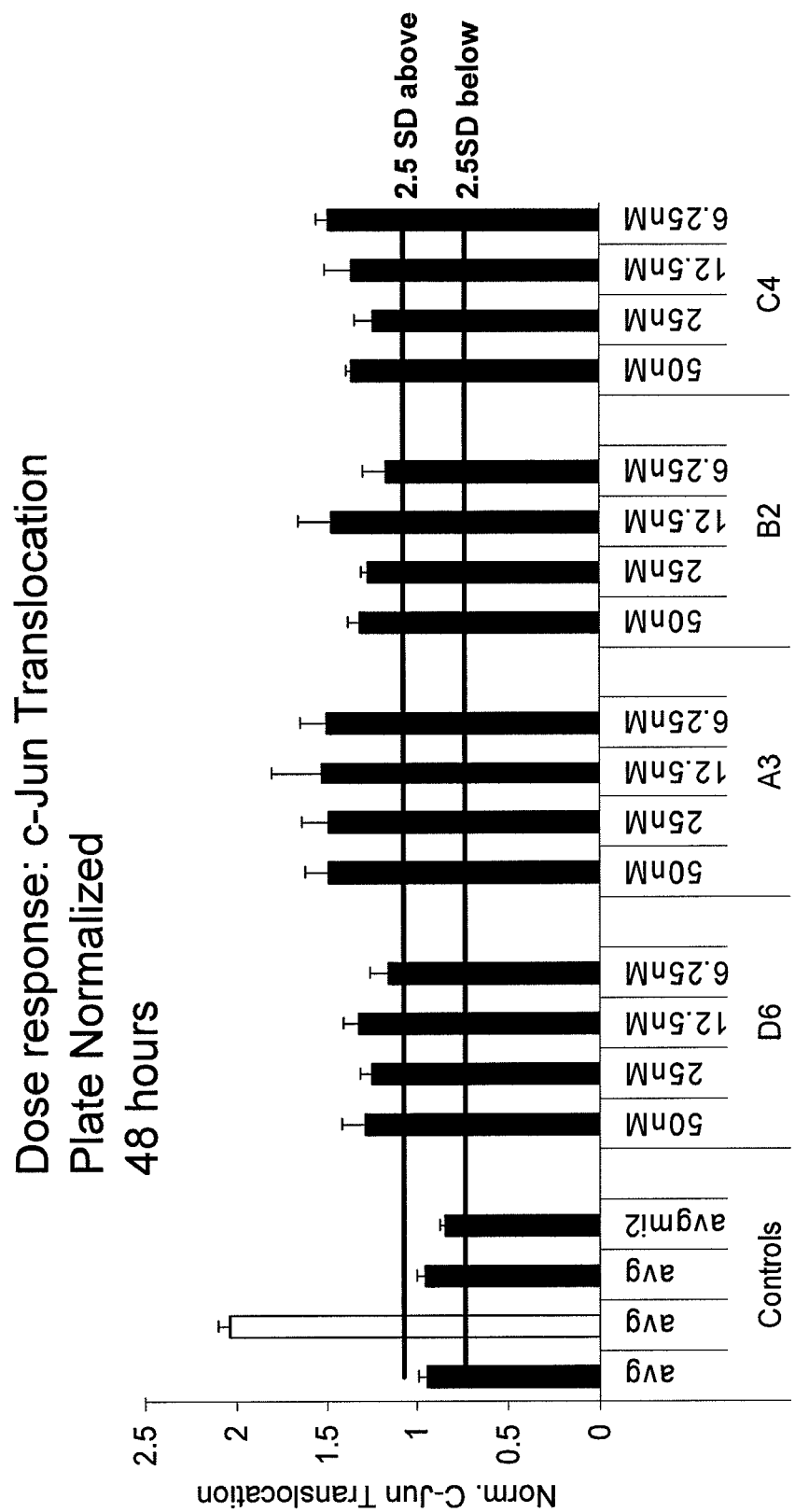
FIG. 13 shows normalized data from the dose response curve of the 4 potential hits in the c-Jun translocation phenotype at 48 hrs. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

FIG. 13 shows normalized data from the dose response curve of the 4 potential hits in the c-Jun translocation phenotype at 48 hrs. PLK1 served as the positive control, and miControl 1 and 2 (mi1, mi2) served as the negative controls. The horizontal black lines indicate the values for 2.5 standard deviations above and below, respectively, the average of the negative controls. As seen in the re-screen experiment, all of the potential hits confirm the increase in activated c-Jun. In terms of dose response, there is not dramatic dose responses associated with the hits.

Figure 14:
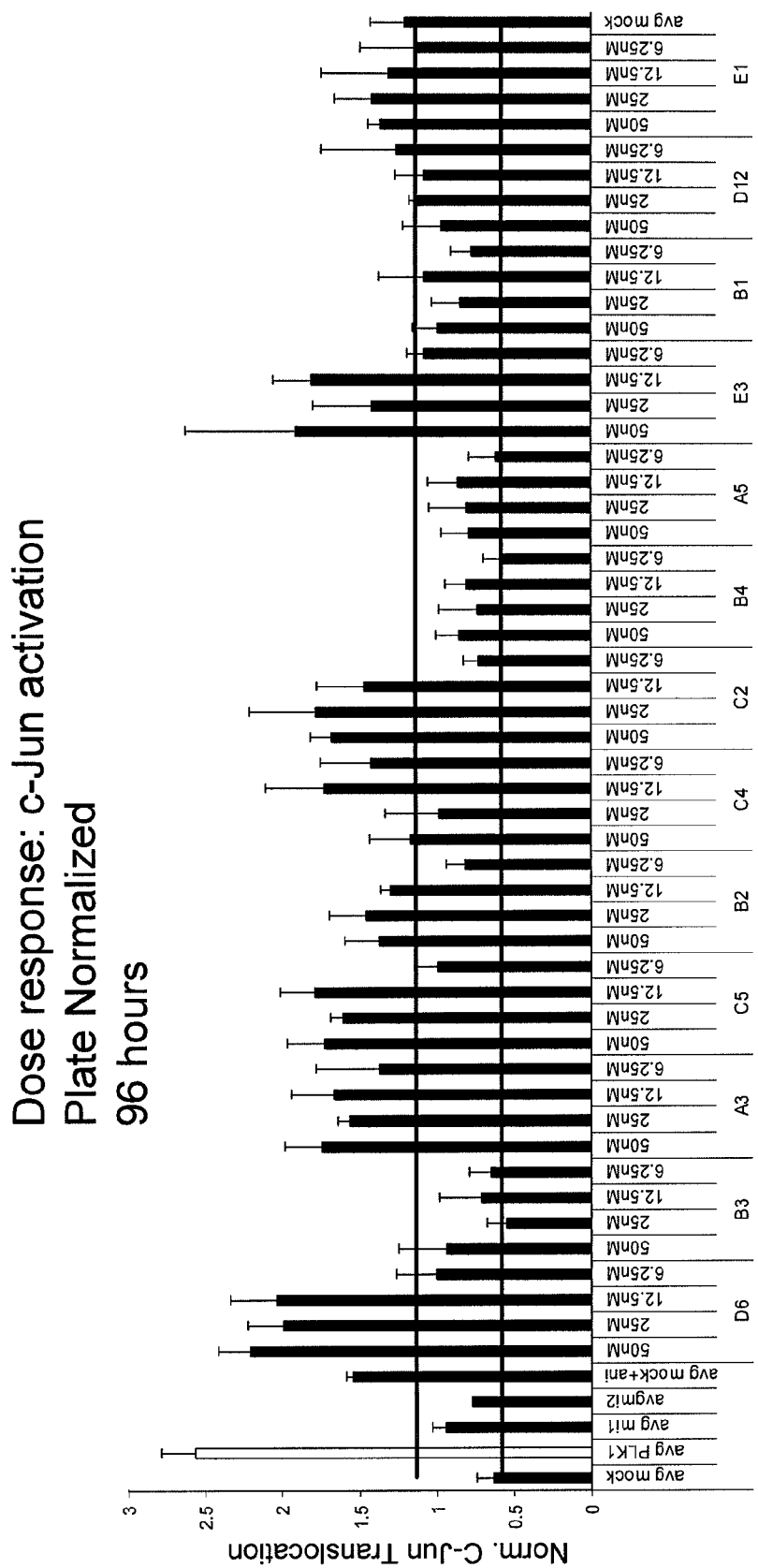
FIG. 14 shows normalized data from the dose response curve of other clusters in the c-Jun translocation phenotype at 96 hrs that were not initially picked up as hits in the original screen. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

FIG. 14 shows normalized data from the dose response curve of other clusters in the c-Jun translocation phenotype at 96 hrs that were not initially picked up as hits in the original screen. PLK1 served as the positive control, and miControl 1 and 2 (mi1, mi2) served as the negative controls. The horizontal black lines indicate the values for 2.5 standard deviations above and below, respectively, the average of the negative controls. At 96 hrs, some clusters have an increased response and effect on c-Jun activation, suggesting there are delayed downstream effects of these inhibitors.

Figure 15:
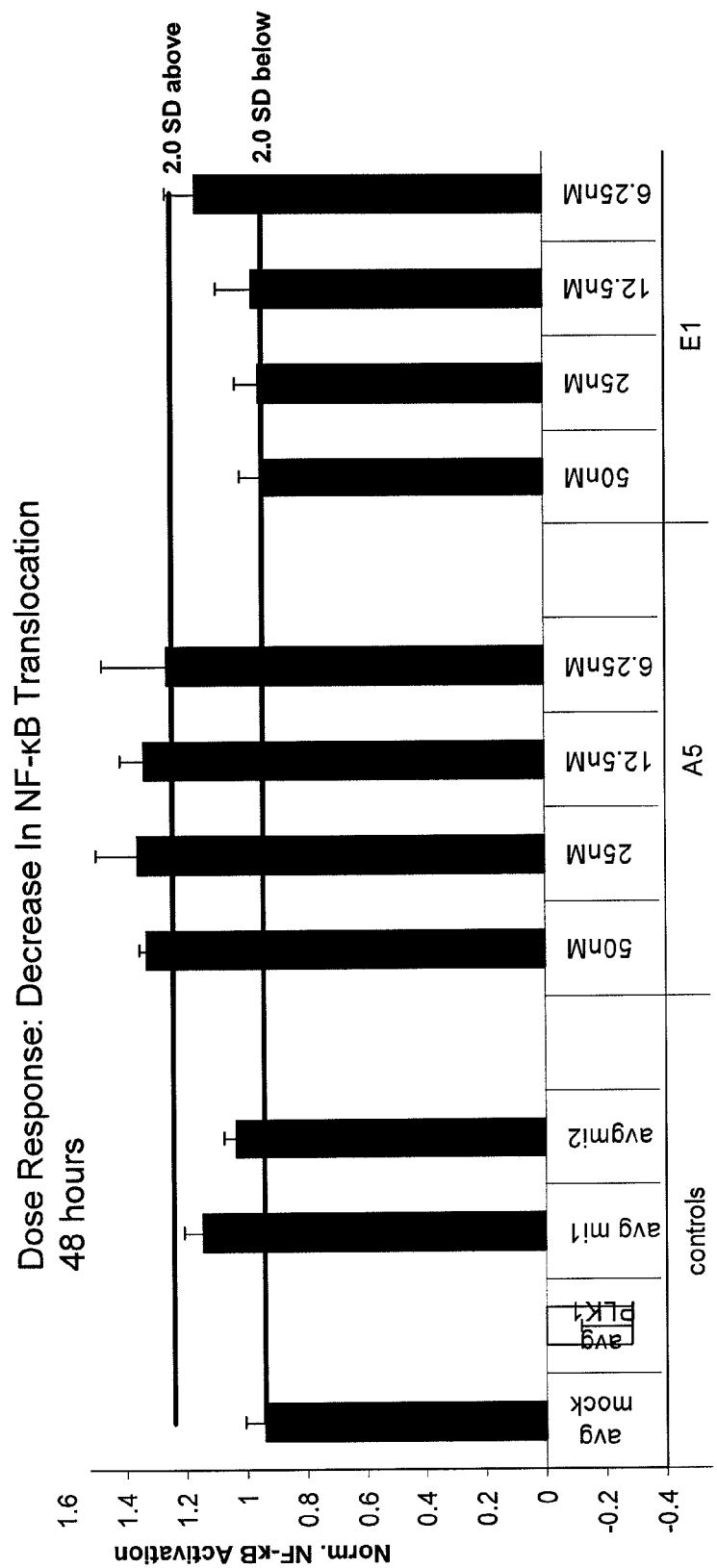
FIG. 15 shows normalized data from the dose response curve of the potential hits in the decrease in NF-κB translocation phenotype at 48 hrs. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

FIG. 15 shows normalized data from the dose response curve of the 2 potential hits in the decrease in NF-κB translocation phenotype at 48 hrs. PLK1 served as the positive control, and miControl 1 and 2 (mi1, mi2) served as the negative controls. The horizontal black lines indicate the values for 2.0 standard deviations above and below, respectively, the average of the negative controls. A5 confirms while E1 does not. There is no dose response seen with these hits either at these concentrations. Contrary to the object count per field and the c-Jun assays, the NF-κB phenotype does not become more dramatic at 96 hrs.

Figure 16:
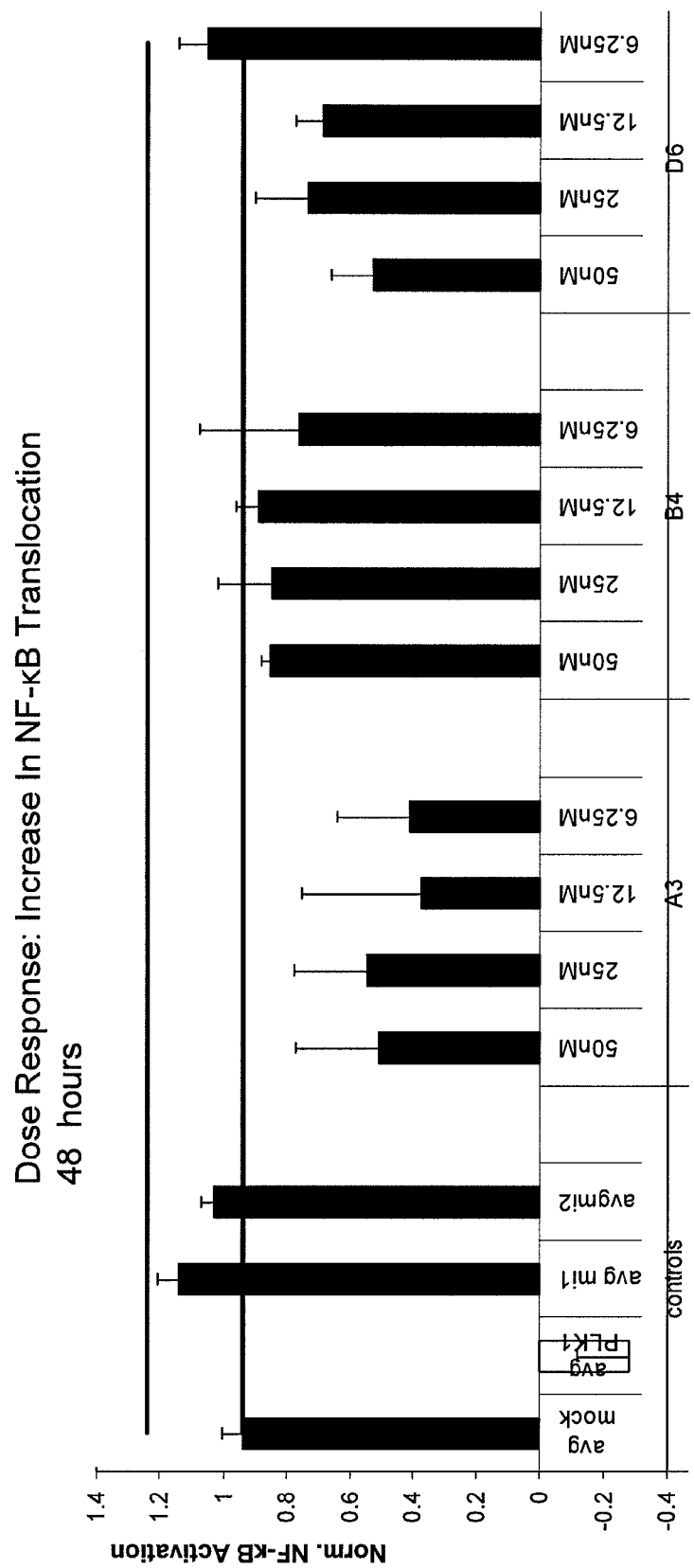
FIG. 16 shows the normalized data from the dose response curve of the potential hits in the increase in NF-κB translocation phenotype at 48 hrs. PLK1 served as the positive control ("avg PLK1"), and miControl 1 and 2 ("avg mi1", "avg mi2") served as the negative controls. The horizontal black lines indicate the values for 2.5 standard deviations above and below, respectively, the average of the negative controls.

FIG. 16 shows the normalized data from the dose response curve of the potential hits in the increase in NF-κB translocation phenotype at 48 hrs. PLK1 served as the positive control, and miControl 1 and 2 (mi1, mi2) served as the negative controls. The horizontal black lines indicate the values for 2.0 standard deviations above and below, respectively, the average of the negative controls. All hits confirm. There is not a dramatic dose response seen with these hits (maybe for D6) at these concentrations. Contrary to the object count per field and the c-Jun assays, the NF-κB phenotype does not become more dramatic at 96 hrs.

FIG. 17 provides a summary of the hits and the phenotypes they are associated with when inhibited. Cluster pool inhibition of the D6 miRNA cluster (miR-17-5p, 18a, 19a, 20a, 19b, and 92) and the A3 miRNA cluster (miR-93, 106b, 25) leads to particularly clear phenotypes in all three assays: a decrease in object count per field, an increase in c-Jun translocation, and an increase in NF-κB translocation. Functional reporter data (using Fluc and Rluc) and microarray data indicate that the D6 cluster and the A3 cluster are endogenously expressed in MCF7 cells (data not shown). Some of the cluster members share seeds. The D6 cluster is known as the cancer cluster and has been implicated in a variety of cancers, suggesting that it acts as a tumor promoter. Thus, inhibition of the cluster may promote apoptosis. The D6 and A3 cluster are associated in that they are part of an ancient microRNA cluster.

Figure 18:
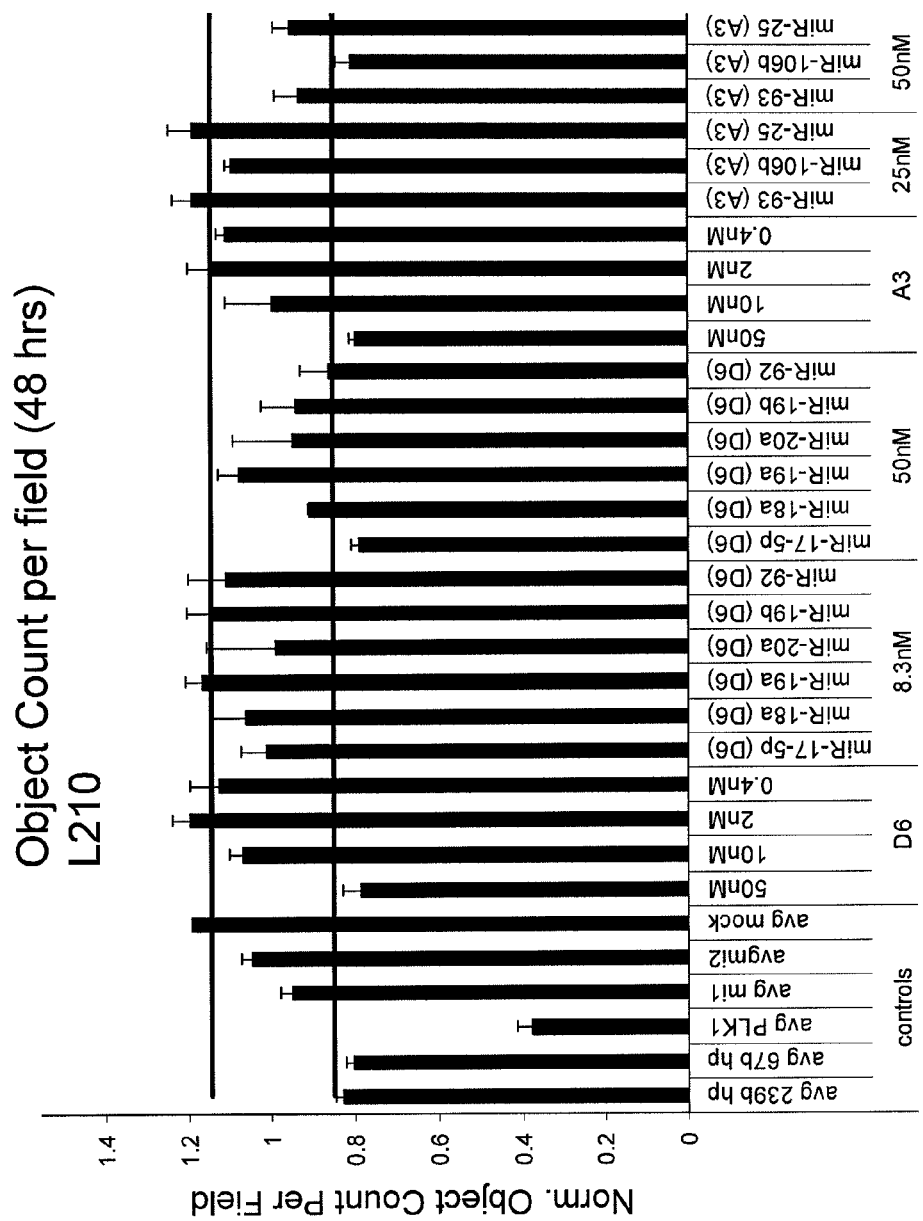
FIG. 18 shows analysis of individual inhibitors compared to the cluster pool using object count per field.

FIG. 18 shows analysis of individual inhibitors compared to the cluster pool using object count per field. The results show that the mir-17-5p inhibitor shows the same phenotype as the D6 cluster pool and the mir106b inhibitor shows the same phenotype as the A3 cluster pool. In addition, a wider dose curve was performed on the clusters.

What is claimed is:

1. A method for screening a cell for at least one phenotype resulting from inhibition of a miRNA cluster, wherein said at least one phenotype is selected from the group consisting of increased cell death, decreased cell death, increased c-Jun nuclear translocation, decreased c-Jun nuclear translocation, increased NF-κB nuclear translocation, and decreased NF-κB nuclear translocation, and the miRNA cluster comprises miR-106b and at least one miRNA selected from the group consisting of miR-93 and miR-25, the method comprising:
   (a) introducing into said cell a cluster pool comprising at least one miRNA inhibitor specific for each miRNA in said miRNA cluster, wherein each miRNA inhibitor comprises a sequence that is at least partially the reverse complement of a mature miRNA sequence and flanking sequences located 5' and 3' to the sequence, wherein the flanking sequences are the reverse complements of sequences that are adjacent to the mature miRNA in a native pri-miRNA; and
   (b) determining whether said cell manifests said at least one phenotype.

2. The method of claim 1 further comprising:
   (c) determining whether said at least one phenotype can be recapitulated in said cell by an individual miRNA inhibitor from said pool by:
      (i) introducing into said cell an individual miRNA inhibitor from said cluster pool; and
      (ii) determining whether said cell manifests said at least one phenotype.

3. The method of claim 2 wherein step (c)(i) is performed at a plurality of different concentrations of said individual miRNA inhibitor.

4. The method of claim 1 wherein said at least one phenotype is determined using High Content Screening (HCS).

5. The method of claim 1 wherein said cell is a breast cancer cell.

6. The method of claim 5 wherein said breast cancer cell is a MCF7 cell.

7. The method of claim 1, wherein the miRNA cluster comprises miR-93.

8. The method of claim 1, wherein the miRNA cluster comprises miR-25.

9. The method of claim 1, wherein the miRNA cluster comprises miR-93 and miR-25.

10. The method of claim 2, wherein in (c)(i) said individual inhibitor inhibits miR-106b.

* * * * *

SEQUENCE LISTING

<160> NUMBER OF SEQ ID NOS: 30

<210> SEQ ID NO 1
<211> LENGTH: 24
<212> TYPE: RNA
<213> ORGANISM: Homo sapien

<400> SEQUENCE: 1
caaagugcuu acagugcagg uagu        24

```
<210> SEQ ID NO 2
<211> LENGTH: 22
<212> TYPE: RNA
<213> ORGANISM: Homo sapien

<400> SEQUENCE: 2
uaaggugcau cuagugcaga ua                                              22

<210> SEQ ID NO 3
<211> LENGTH: 23
<212> TYPE: RNA
<213> ORGANISM: Homo sapien

<400> SEQUENCE: 3
ugugcaaauc uaugcaaaac uga                                             23

<210> SEQ ID NO 4
<211> LENGTH: 23
<212> TYPE: RNA
<213> ORGANISM: Homo sapien

<400> SEQUENCE: 4
uaaagugcuu auagugcagg uag                                             23

<210> SEQ ID NO 5
<211> LENGTH: 23
<212> TYPE: RNA
<213> ORGANISM: Homo sapien

<400> SEQUENCE: 5
ugugcaaauc caugcaaaac uga                                             23

<210> SEQ ID NO 6
<211> LENGTH: 21
<212> TYPE: RNA
<213> ORGANISM: Homo sapien

<400> SEQUENCE: 6
uauugcacuu gucccggccu g                                               21

<210> SEQ ID NO 7
<211> LENGTH: 22
<212> TYPE: RNA
<213> ORGANISM: Homo sapien

<400> SEQUENCE: 7
aaagugcugu ucgugcaggu ag                                              22

<210> SEQ ID NO 8
<211> LENGTH: 21
<212> TYPE: RNA
<213> ORGANISM: Homo sapien

<400> SEQUENCE: 8
uaaagugcug acagugcaga u                                               21

<210> SEQ ID NO 9
<211> LENGTH: 22
<212> TYPE: RNA
<213> ORGANISM: Homo sapien

<400> SEQUENCE: 9
cauugcacuu gucucggucu ga                                              22
```

```
<210> SEQ ID NO 10
<211> LENGTH: 20
<212> TYPE: RNA
<213> ORGANISM: Homo sapien

<400> SEQUENCE: 10
uguaaacauc cuugacugga                                             20

<210> SEQ ID NO 11
<211> LENGTH: 23
<212> TYPE: RNA
<213> ORGANISM: Homo sapien

<400> SEQUENCE: 11
uguaaacauc cuacacucuc agc                                         23

<210> SEQ ID NO 12
<211> LENGTH: 21
<212> TYPE: RNA
<213> ORGANISM: Homo sapien

<400> SEQUENCE: 12
uagcagcaca gaaauauugg c                                           21

<210> SEQ ID NO 13
<211> LENGTH: 21
<212> TYPE: RNA
<213> ORGANISM: Homo sapien

<400> SEQUENCE: 13
cagcagcaca cuguguuug u                                            21

<210> SEQ ID NO 14
<211> LENGTH: 22
<212> TYPE: RNA
<213> ORGANISM: Homo sapien

<400> SEQUENCE: 14
uagcagcaca uaaugguuug ug                                          22

<210> SEQ ID NO 15
<211> LENGTH: 22
<212> TYPE: RNA
<213> ORGANISM: Homo sapien

<400> SEQUENCE: 15
uagcagcacg uaaauauugg cg                                          22

<210> SEQ ID NO 16
<211> LENGTH: 22
<212> TYPE: RNA
<213> ORGANISM: Homo sapien

<400> SEQUENCE: 16
uaauacugcc ugguaaugau ga                                          22

<210> SEQ ID NO 17
<211> LENGTH: 22
<212> TYPE: RNA
<213> ORGANISM: Homo sapien

<400> SEQUENCE: 17
uaacacuguc ugguaacgau gu                                          22
```

```
<210> SEQ ID NO 18
<211> LENGTH: 22
<212> TYPE: RNA
<213> ORGANISM: Homo sapien

<400> SEQUENCE: 18
uaauacuguc ugguaaaacc gu                                              22

<210> SEQ ID NO 19
<211> LENGTH: 22
<212> TYPE: RNA
<213> ORGANISM: Homo sapien

<400> SEQUENCE: 19
uguaaacauc cuacacucag cu                                              22

<210> SEQ ID NO 20
<211> LENGTH: 22
<212> TYPE: RNA
<213> ORGANISM: Homo sapien

<400> SEQUENCE: 20
uguaaacauc cccgacugga ag                                              22

<210> SEQ ID NO 21
<211> LENGTH: 22
<212> TYPE: RNA
<213> ORGANISM: Homo sapien

<400> SEQUENCE: 21
uaacacuguc ugguaaagau gg                                              22

<210> SEQ ID NO 22
<211> LENGTH: 23
<212> TYPE: RNA
<213> ORGANISM: Homo sapien

<400> SEQUENCE: 22
uaauacugcc ggguaaugau gga                                             23

<210> SEQ ID NO 23
<211> LENGTH: 21
<212> TYPE: RNA
<213> ORGANISM: Homo sapien

<400> SEQUENCE: 23
auccuugcua ucugggugcu a                                               21

<210> SEQ ID NO 24
<211> LENGTH: 22
<212> TYPE: RNA
<213> ORGANISM: Homo sapien

<400> SEQUENCE: 24
aauccuuugu cccuggguga ga                                              22

<210> SEQ ID NO 25
<211> LENGTH: 22
<212> TYPE: RNA
<213> ORGANISM: Homo sapien

<400> SEQUENCE: 25
augcaccugg gcaaggauuc ug                                              22
```

```
<210> SEQ ID NO 26
<211> LENGTH: 24
<212> TYPE: RNA
<213> ORGANISM: Homo sapien

<400> SEQUENCE: 26
aauccuugga accuaggugu gagu                                          24

<210> SEQ ID NO 27
<211> LENGTH: 22
<212> TYPE: RNA
<213> ORGANISM: Homo sapien

<400> SEQUENCE: 27
caucccuugc augguggagg gu                                            22

<210> SEQ ID NO 28
<211> LENGTH: 22
<212> TYPE: RNA
<213> ORGANISM: Homo sapien

<400> SEQUENCE: 28
caaucacuaa cuccacugcc au                                            22

<210> SEQ ID NO 29
<211> LENGTH: 23
<212> TYPE: RNA
<213> ORGANISM: Homo sapien

<400> SEQUENCE: 29
aggcagugua guuagcugau ugc                                           23

<210> SEQ ID NO 30
<211> LENGTH: 10
<212> TYPE: DNA
<213> ORGANISM: Homo sapien

<400> SEQUENCE: 30
gggactttcc                                                          10
```